(12) United States Patent
Lennartz et al.

(10) Patent No.: US 11,832,916 B2
(45) Date of Patent: Dec. 5, 2023

(54) SYSTEM AND METHODS FOR IDENTIFYING VESSELS WITHIN TISSUE

(71) Applicant: Covidien LP, Mansfield, MA (US)

(72) Inventors: Amanda H. Lennartz, Erie, CO (US); Daniel A. Joseph, Golden, CO (US); Cornelia F. Twomey, Longmont, CO (US); Erin E. Wehrly, Longmont, CO (US); David M. Garrison, Longmont, CO (US); Tyler J. Bagrosky, Arvada, CO (US); Robert H. Wham, Boulder, CO (US); Jing Zhao, Superior, CO (US); Tracy J. Pheneger, Longmont, CO (US)

(73) Assignee: Covidien LP, Mansfield, MA (US)

( * ) Notice: Subject to any disclaimer, the term of this patent is extended or adjusted under 35 U.S.C. 154(b) by 378 days.

(21) Appl. No.: 17/112,298

(22) Filed: Dec. 4, 2020

(65) Prior Publication Data

US 2021/0228087 A1    Jul. 29, 2021

Related U.S. Application Data

(60) Provisional application No. 62/967,246, filed on Jan. 29, 2020, provisional application No. 62/967,238, (Continued)

(51) Int. Cl.
*A61B 5/00* (2006.01)
*A61B 34/10* (2016.01)
(Continued)

(52) U.S. Cl.
CPC ............ *A61B 5/0082* (2013.01); *A61B 5/489* (2013.01); *A61B 17/320092* (2013.01);
(Continued)

(58) Field of Classification Search
CPC .......... A61B 17/320092; A61B 18/085; A61B 18/1445; A61B 18/1482; A61B 18/18;
(Continued)

(56) References Cited

U.S. PATENT DOCUMENTS 4,502,487 A    3/1985 DuBrucq et al.
5,460,182 A    10/1995 Goodman et al.
(Continued)

FOREIGN PATENT DOCUMENTS

EP    3505076 A2    7/2019

OTHER PUBLICATIONS

International Search Report and Written Opinion issued by the International Searching Authority in International Application No. PCT/US2020/063327 dated Mar. 29, 2021.

*Primary Examiner* — Mark D Remaly
(74) *Attorney, Agent, or Firm* — Carter, DeLuca & Farrell LLP

(57) ABSTRACT

A method includes providing a graphical representation of a surgical site, grasping the tissue of the patient with first and second jaw members of an end effector including a location sensor, illuminating optical light into the grasped tissue at the first jaw member, receiving the optical light that has passed through the grasped tissue, at the second jaw member, processing the received light to identify a vessel, which is encompassed within the grasped tissue, receiving location information of the end effector from the location sensor, synchronizing a location of the identified vessel within the graphical representation based on the location information, and displaying the identified vessel at the synchronized location in the graphical representation.

11 Claims, 14 Drawing Sheets

Related U.S. Application Data filed on Jan. 29, 2020, provisional application No. 62/967,241, filed on Jan. 29, 2020.

(51) Int. Cl.

| | |
|---|---|
| *A61B 17/32* | (2006.01) |
| *A61B 18/08* | (2006.01) |
| *A61B 18/14* | (2006.01) |
| *A61B 18/18* | (2006.01) |
| *A61B 34/00* | (2016.01) |
| A61B 17/00 | (2006.01) |
| A61B 18/00 | (2006.01) |
| A61B 6/03 | (2006.01) |
| A61B 6/00 | (2006.01) |
| A61B 8/08 | (2006.01) |

(52) U.S. Cl.
CPC ........ *A61B 18/085* (2013.01); *A61B 18/1445* (2013.01); *A61B 18/18* (2013.01); *A61B 34/10* (2016.02); *A61B 34/25* (2016.02); *A61B 5/0075* (2013.01); *A61B 6/032* (2013.01); *A61B 6/504* (2013.01); *A61B 8/085* (2013.01); *A61B 2017/00778* (2013.01); *A61B 2017/320095* (2017.08); *A61B 2018/0063* (2013.01); *A61B 2018/00404* (2013.01); *A61B 2018/00535* (2013.01); *A61B 2018/00642* (2013.01); *A61B 2018/00791* (2013.01); *A61B 2018/00827* (2013.01); *A61B 2018/00875* (2013.01); *A61B 2018/00892* (2013.01); *A61B 2018/00904* (2013.01); *A61B 2018/00982* (2013.01); *A61B 2018/1452* (2013.01); *A61B 2018/1807* (2013.01); *A61B 2034/105* (2016.02)

(58) Field of Classification Search
CPC ........... A61B 2017/00057; A61B 2017/00084; A61B 2017/00115; A61B 2017/00778; A61B 2017/320095; A61B 2018/00404; A61B 2018/00535; A61B 2018/0063; A61B 2018/00642; A61B 2018/00791; A61B 2018/00827; A61B 2018/00875; A61B 2018/00892; A61B 2018/00904; A61B 2018/00982; A61B 2018/1452; A61B 2018/1807; A61B 2034/105; A61B 2034/2051; A61B 2090/365; A61B 2090/3762; A61B 34/10; A61B 34/25; A61B 5/0075; A61B 5/0082; A61B 5/0084; A61B 5/489; A61B 5/6847; A61B 6/032; A61B 6/504; A61B 8/085; A61B 90/37

See application file for complete search history.

(56) References Cited

U.S. PATENT DOCUMENTS

| | | |
|---|---|---|
| 5,494,045 A | 2/1996 | Kiviranta et al. |
| 6,030,384 A | 2/2000 | Nezhat |
| 6,071,242 A | 6/2000 | Lin |
| 6,190,353 B1 | 2/2001 | Makower et al. |
| 6,723,092 B2 | 4/2004 | Brown et al. |
| 7,625,370 B2 | 12/2009 | Hart et al. |
| 7,731,717 B2 | 6/2010 | Odom et al. |
| 7,776,037 B2 | 8/2010 | Odom |
| 8,216,235 B2 | 7/2012 | Rioux et al. |
| 8,382,754 B2 | 2/2013 | Odom et al. |
| 8,439,913 B2 | 5/2013 | Horner et al. |
| 9,149,260 B2 | 10/2015 | Stone et al. |
| 9,173,698 B2 | 11/2015 | Van Lue et al. |
| 9,247,988 B2 | 2/2016 | McKenna et al. |
| 9,375,259 B2 | 6/2016 | Payne et al. |
| 9,420,983 B2 | 8/2016 | Zagorchev et al. |
| 9,603,652 B2 | 3/2017 | Carlton et al. |
| 9,642,665 B2 | 5/2017 | Weinberg et al. |
| 9,693,816 B2 | 7/2017 | Orszulak |
| 9,839,467 B2 | 12/2017 | Harper et al. |
| 9,918,783 B2 | 3/2018 | Horner et al. |
| 10,117,705 B2 | 11/2018 | Chernov et al. |
| 10,130,413 B2 | 11/2018 | Brandt et al. |
| 10,143,533 B2 | 12/2018 | Park |
| 10,188,448 B2 | 1/2019 | Friedrichs |
| 10,245,104 B2 | 4/2019 | McKenna et al. |
| 10,335,226 B2 | 7/2019 | Harper et al. |
| 10,893,899 B2 | 1/2021 | Weber |
| 2003/0225324 A1 | 12/2003 | Anderson et al. |
| 2005/0043623 A1 | 2/2005 | Jurvelin et al. |
| 2006/0116572 A1 | 6/2006 | Case |
| 2009/0028793 A1 | 1/2009 | Neri et al. |
| 2009/0204114 A1 | 8/2009 | Odom |
| 2010/0069941 A1 | 3/2010 | Cohen et al. |
| 2010/0152586 A1 | 6/2010 | Grant et al. |
| 2010/0217264 A1 | 8/2010 | Odom et al. |
| 2010/0331838 A1 | 12/2010 | Ibrahim et al. |
| 2011/0009899 A1 | 1/2011 | Picha Muthu et al. |
| 2011/0112570 A1 | 5/2011 | Mannava et al. |
| 2012/0041345 A1 | 2/2012 | Rajamani et al. |
| 2012/0296205 A1 | 11/2012 | Chernov et al. |
| 2013/0171649 A1 | 7/2013 | Mayr |
| 2015/0088125 A1 | 3/2015 | Wham |
| 2015/0122870 A1 | 5/2015 | Zemlok et al. |
| 2015/0223868 A1 | 8/2015 | Brandt et al. |
| 2016/0045248 A1 | 2/2016 | Unger et al. |
| 2016/0089198 A1 | 3/2016 | Arya et al. |
| 2016/0174998 A1 | 6/2016 | Lal et al. |
| 2016/0346034 A1 | 12/2016 | Arya et al. |
| 2017/0035929 A1 | 2/2017 | Phillips et al. |
| 2017/0061621 A1 | 3/2017 | Wortman |
| 2017/0079740 A1 | 3/2017 | Hufnagel et al. |
| 2017/0215943 A1 | 8/2017 | Allen, IV |
| 2017/0215944 A1 | 8/2017 | Keffeler |
| 2017/0252479 A1 | 9/2017 | Ji et al. |
| 2017/0265831 A1 | 9/2017 | Sankaran et al. |
| 2017/0319190 A1 | 11/2017 | Rooks |
| 2017/0372474 A1 | 12/2017 | Behar et al. |
| 2019/0019347 A1 | 1/2019 | Auvray et al. |
| 2019/0057541 A1 | 2/2019 | Li et al. |
| 2019/0083168 A1 | 3/2019 | Wham |
| 2019/0282296 A1 | 9/2019 | Harper et al. |
| 2020/0237423 A1* | 7/2020 | Witte ................. A61G 13/1235 |

\* cited by examiner

SYSTEM AND METHODS FOR IDENTIFYING VESSELS WITHIN TISSUE

CROSS-REFERENCE TO RELATED APPLICATIONS

This application claims the benefit of and priority to U.S. Provisional patent Application Nos. 62/967,238; 62/967,241; and 62/967,246, filed on Jan. 29, 2020, the entire contents of each of which is hereby incorporated herein by reference.

FIELD

The present disclosure is generally related to systems and methods for identifying a location of vessel within tissue with a light source, displaying the identified vessel at a proper location, and/or confirming sealing of the identified vessel.

BACKGROUND

Surgical operations including laparoscopic operations involve operations on tissue. During an operation, tissue can be cut, coagulated, and/or sealed. Complications may occur when the tissue includes vessels, such as blood, vile, or lymph vessels. For example, when tissue is planned to be cut and the tissue includes a blood vessel, the blood vessel might also be also cut and leak blood or body fluid around the tissue, thereby causing complications. Thus, identification of vessels, which are not seen from outside or are hidden within the tissue, is advantageous.

During laparoscopic operations, a surgeon has a limited view. Thus, display of hidden vessels at an appropriate place on a display is also advantageous in increasing certainty of efficacy of the surgical operations and decreasing potential harm to patients.

Further, prior to or concurrently with surgical operations, completion of sealing of vessel needs to be confirmed so as to also increase certainty of efficacy of the surgical operations and decrease potential harm to patients.

SUMMARY

This disclosure generally relates to identification of vessels hidden within tissue, display of the identified vessels at the proper location, and/or confirmation of sealing of vessels so that performance and efficacy of surgical operations can be increased.

Provided in accordance with aspects of the disclosure is a method for identifying a vessel within tissue. The method includes providing a graphical representation of a surgical site, grasping the tissue of the patient with first and second jaw members of an end effector including a location sensor, illuminating optical light into the grasped tissue at the first jaw member, receiving the optical light that has passed through the grasped tissue, at the second jaw member, processing the received light to identify a vessel, which is encompassed within the grasped tissue, receiving location information of the end effector from the location sensor, synchronizing a location of the identified vessel within the graphical representation based on the location information, and displaying the identified vessel at the synchronized location in the graphical representation.

In an aspect of the disclosure, the method further includes supplying energy to the tissue through the end effector to seal the identified vessel, illuminating the optical light into the identified vessel after supplying the energy, and receiving the optical light that has passed through the identified vessel.

In an aspect of the disclosure, the method further includes processing the received optical light after supplying the energy.

In another aspect of the disclosure, the method further includes confirming whether or not the identified vessel is sealed. The identified vessel is confirmed to be sealed by comparing the identified vessel before supplying the energy with the identified vessel after supplying the energy.

In still another aspect of the disclosure, the graphical representation is a 3D model or a video image.

In still another aspect of the disclosure, the vessel is selected from the group consisting of a bile vessel, a lymph vessel, and a blood vessel.

In yet another aspect of the disclosure, the method further includes generating an electromagnetic wave. In another aspect, the method further includes sensing the electromagnetic wave. The location information is based on the sensed electromagnetic wave.

In yet still another aspect of the disclosure, the identified vessel is displayed in an augmented manner in the graphical representation.

Provided in accordance with aspects of the disclosure is a system for identifying a vessel within tissue. The system includes an end effector configured to grasp tissue, the end effector including a first jaw member and a second jaw member, an optical light source configured to emit optical light to the grasped tissue and fixed at the first jaw member, a light sensor configured to receive the optical light that has passed through the grasped tissue, and fixed at the second jaw member, a location sensor configured to detect location information of the end effector, a processor configured to receive a graphical representation of a surgical site, process the received light to identify a vessel, which is encompassed within the grasped tissue, and synchronize a location of the identified vessel within the graphical representation based on the location information, and a display configured to display the identified vessel at the synchronized location in the graphical representation.

In an aspect of the disclosure, the system further includes an energy supplier configured to supply energy through the end effector to seal the identified vessel. The optical light source is further configured to illuminate the optical light into the identified vessel after supplying the energy, and the location sensor is further configured to receive the optical light that has passed through the identified tissue.

In another aspect of the disclosure, the processor is further configured to process the received light after supplying the energy.

In another aspect of the disclosure, the processor is further configured to confirm whether or not the identified vessel is sealed.

In another aspect of the disclosure, the processor confirms that the identified vessel is sealed by comparing the identified vessel before supplying the energy with the identified vessel after supplying the energy. The graphical representation is a three-dimensional model or a video image.

In another aspect of the disclosure, the vessel is selected from the group consisting of a bile vessel, a lymph vessel, and a blood vessel.

In still another aspect of the disclosure, the system further includes an electromagnetic wave generator configured to generate an electromagnetic wave.

In yet another aspect of the disclosure, the system further includes an electromagnetic sensor configured to sense the electromagnetic wave. The location information is based on the sensed electromagnetic wave.

In yet still another aspect of the disclosure, the identified vessel is displayed in an augmented manner in the graphical representation.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
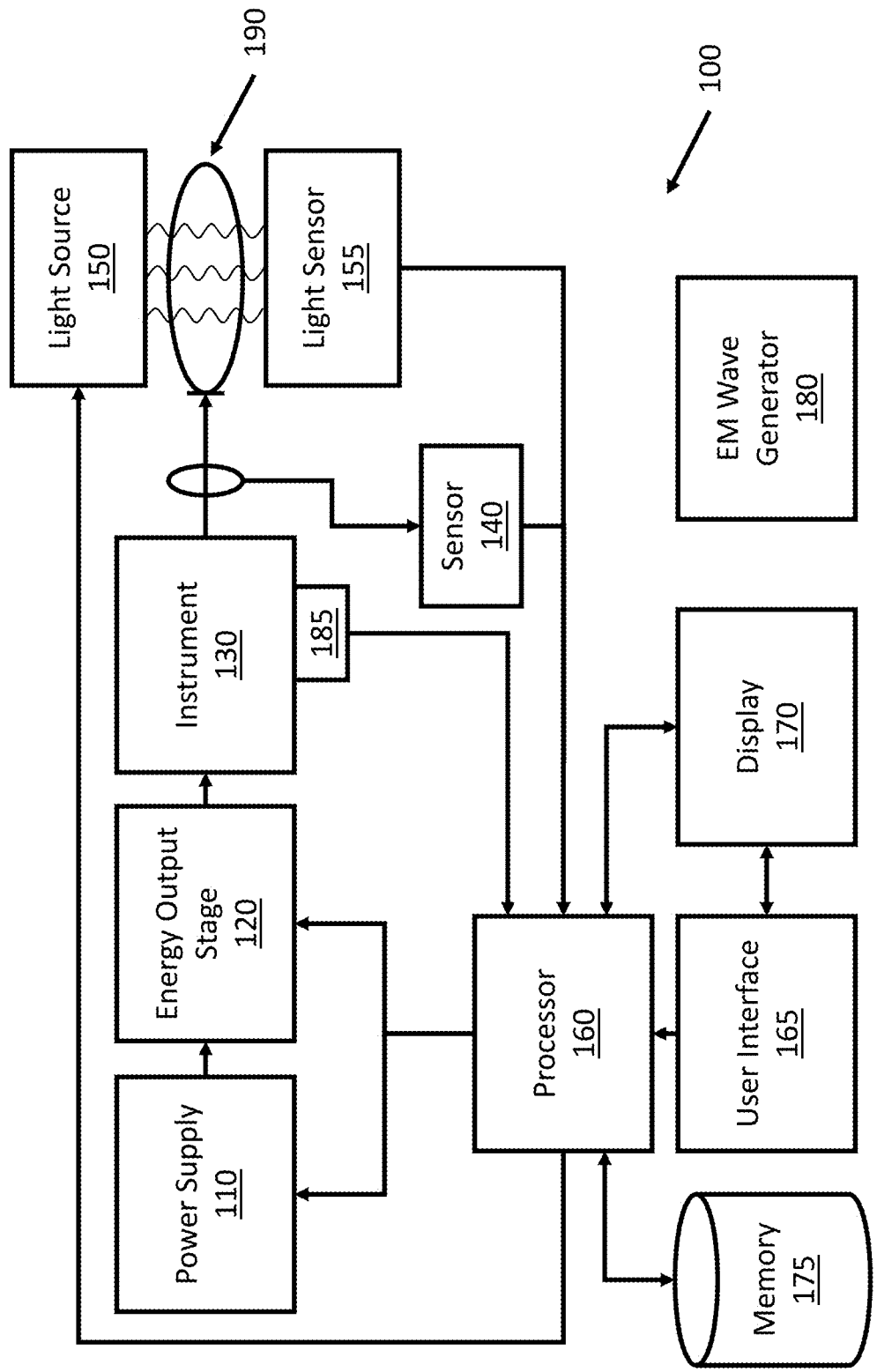
FIG. 1 is a block diagram of a surgical system for identifying vessels according to aspects of the present disclosure.

Surgical operations often involve operations to tissue that includes vessels. When the tissue is to be cut or treated, the vessels in the tissue should be sealed so as to prevent blood or body fluid from leaking. Thus, identification of the vessels in the tissue enhances performance of the surgical operations. Further, prior to, concurrently with, or after the treatment of the tissue, completeness of sealing vessels should be confirmed. Thus, the present disclosure provides systems and methods for identifying vessels, which are hidden within tissue, displaying the identified vessel at an appropriate location, and/or confirming completeness of the vessel seal.

Different types of light sources and light sensors may be used to identify a location of a vessel. For example, an optical light source or laser light source is employed in this disclosure, although other light sources are also contemplated. Identification of vessels may be based on optical light, reflected laser spectrum, Raman shift, or in any other suitable manner. Corresponding structures and methods are described in the following description and in the drawings.

FIG. 1 shows a block diagram of a surgical system 100 for identifying vessels according to embodiments of the present disclosure. The surgical system 100 may use any type of energy to seal tissue including mechanical energy, acoustic energy, thermal energy, electrical energy, or electromagnetic (EM) energy (e.g., optical energy or radio frequency (RF) energy). The surgical system 100 may use EM waves to identify a location of one or more elements of the surgical system 100 and synchronize the patient with a three-dimensional (3D) model of a patient. Ultrasound may be used by the surgical system 100 to identify a location of elements of the surgical system 100. Further, the surgical system 100 may identify a location of vessels hidden in tissue of interest, synchronize the identified location of the vessel with the 3D model, and display a graphical representation of the vessel at the corresponding location in the 3D model in an augmented way. By doing the above, the surgical system 100 helps clinicians to perform surgical operations without unintentionally cutting or otherwise damaging vessels, e.g., blood vessels.

In embodiments, the surgical system 100 may use EM waves to identify a location of one or more elements of the surgical system 100 and synchronize the patient with a live video of a patient. Further, the surgical system 100 may identify a location of vessels hidden in tissue of interest, synchronize the identified location of the vessel with the live video, and display a graphical representation of the vessel at the corresponding location in the live video in an augmented way. By doing the above, the surgical system 100 helps clinicians to perform surgical operations without unintentionally cutting or otherwise damaging vessels, e.g., blood vessels.

Prior to or concurrently with surgical operations, a three-dimensional (3D) model is generated to visually display patient's anatomy. During an imaging/planning stage, a computer utilizes computed tomography (CT) image data or other image data in the Digital Imaging and Communications in Medicine (DICOM) format or similar format, for generating and viewing a 3D model of the patient's body. In embodiments, the 3D model may be generated in real time based on the live video. The 3D model and image data derived from the 3D model enables identification of the region of interest (automatically, semi-automatically or manually), and allows for the selection of a pathway to the region of interest. More specifically, the CT scans are processed and assembled into a 3D volume, which is then utilized to generate the 3D model of the patient's body. The surgical system 100 may include a memory 175 to store the 3D model or receive the 3D model from another computer, which has generated or stored the 3D model. The surgical system 100 may be coupled to a display 170 and cause the display 170 to display the 3D model on its screen.

The surgical system 100 may include a power supply 110, an energy output stage 120, and an instrument 130. The power supply 110 supplies power to the energy output stage 120, which generates energy and provides the energy to the instrument 130. The instrument 130, in turn, applies the generated energy to the tissue 190, which includes at least one vessel. For an RF-based tissue-sealing system, the energy output stage 120 generates RF energy and the instrument 130 applies the RF energy to the tissue 190 through at least one contact to seal the tissue 190. Various other types of instruments 130 may be encompassed in this disclosure as understood by a person having ordinary skill in the art.

The surgical system 100 may also include a sensor 140, a processor 160, a user interface 165, and display 170. The sensor 140 senses various parameters and/or properties of the RF energy applied by the instrument 130 at the operating site and transmits sensor signals representing the sensed parameters or properties of the RF energy to the processor 160. The processor 160 processes the sensor signals and generates control signals based on the processed sensor signals to control the power supply 110 and/or the energy output stage 120. For example, the processor 160 may regulate the voltage or current output from the power supply 110 or the energy output stage 120 based on the processed sensor signals.

The sensor 140 is configured to measure various electrical or electromechanical conditions at the operating site such as tissue impedance, changes in tissue impedance, tissue temperature, changes in tissue temperature, leakage current, applied voltage, and applied current. The sensor 140 may sample, continuously measure, and adjust one or more of these conditions so that the processor 160 can continually adjust the energy output from the power supply 110 and/or the energy output stage 120 during a sealing procedure. For example, in an RF-based vessel sealing, the sensor 140 may measure tissue impedance and the processor 160 may adjust the voltage generated by the energy output stage 120.

The user interface 165 is coupled to the processor 160 allowing a user to control various parameters of the energy applied to the tissue 190 during a surgical procedure. For example, the user interface 165 may allow a user to manually set, regulate and/or control one or more parameters of the energy delivered to the tissue 190, such as voltage, current, power, frequency, and/or algorithm control parameters, e.g., pulse width, duty cycle, crest factor, and/or repetition rate.

The processor 160 may be designed to execute software instructions, which are saved in the memory 175, for processing data received from the user interface 165 and for outputting control signals to the power supply 110 and/or the energy output stage 120. The software instructions may be uploaded to or stored in an internal memory of the processor 160, an internal or external memory bank accessible by the processor 160 and/or an external memory, e.g., an external hard drive, floppy diskette, or CD-ROM. Control signals generated by the processor 160 may be converted to analog signals by a digital-to-analog converter (DAC) (not shown) before being applied to the power supply 110 and/or energy output stage 120.

For embodiments of an RF-based tissue-sealing system, the power supply 110 is a high-voltage DC power supply that produces RF current. In these embodiments, the processor 160 transmits control signals to the power supply to control the magnitudes of the RF voltage and current output from the power supply 110. The energy output stage 120 receives the RF current and generates one or more algorithm control signals of RF energy. The processor 160 generates algorithm control signals to regulate the parameters of the RF energy, such as pulse width, duty cycle, crest factor, and repetition rate. In other embodiments, the power supply 110 is an AC power supply, and the energy output stage 120 may vary the waveform of the AC signal generated by the power supply 110 to achieve a desired waveform.

As described above, the surgical system 100 includes the user interface 165, which includes an input device, such as a keyboard or touch screen, through which a user enters data and commands. The data may include the type of instrument, the type of procedure, and/or the type of tissue. The commands may include target effective voltage, current, or power level, or other commands for controlling parameters of the energy that is delivered from the energy output stage 120 to the instrument 130.

In embodiments, the user interface 165 may be incorporated into the display 170. For example, the display 170 may be touch sensitive and display graphical icons/representations to adjust various parameters. In such configurations, a clinician adjusts values of the various parameters by touching/holding/dragging icons on the display 170.

The surgical system 100 may also include a light source, e.g., an optical light source 150, and a light sensor 155. The optical light source 150 emits optical light to the tissue 190 and the light sensor 155 senses light, which has passed through or reflected from the tissue 190. In embodiments, the light source 150 may be coupled to the energy output stage 120. The energy output stage 120 may generate light that may be the same as the electrosurgical energy applied to the tissue 190 to perform an electrosurgical procedure (e.g., vessel sealing). Alternatively, the energy output stage 120 may generate light that has parameters that are different from the parameters of the electrosurgical energy applied to the tissue 190.

The light sensor 155 generates a sensor signal or sensor data based on the sensed light and transmits the sensor signal or sensor data to the processor 160, which processes the sensor signal or sensor data to determine the level of blood circulation in the tissue 190 and to identify a location of vessels in the tissue 190. For example, the processor 160 may determine the level of blood circulation and a location of a vessel based on the magnitude, phase, scatter, or Doppler effect of the sensor signal or the sensed light.

The sensed light may also provide information about the tissue type. For example, the sensed light may identify the tissue as connective tissue, muscle tissue, nervous tissue, vascular tissue, epithelial tissue, or any other tissue type or combination of tissue types. The sensed light may also identify the vessel type within the tissue 190. The vessel types include bile vessels, lymph vessels, and blood vessels. The sensed light may distinguish the type of blood vessel that resides in a given portion of tissue. The types of blood vessels include arteries, arterioles, capillaries, venules, and veins. The sensed light may also be used to identify the condition of the tissue, such as whether the tissue is diseased and/or damaged.

The surgical system 100 may determine the level of blood circulation by sensing tissue parameters or properties that depend on the level of blood circulation during a period exceeding one cardiac cycle. In embodiments, the surgical system 100 may sample tissue parameters or properties for multiple cardiac cycles to more accurately determine the level of blood circulation. In other embodiments, a cardiac signal, which is related to heart contractions (e.g., an electrocardiographic signal), can be used to evaluate the correlation between the parameters of the sensor signal and the cardiac signal to more accurately assess the level of blood circulation.

In an embodiment, the light source 150 may emit optical light or radiate laser light. The light sensor 155 may be a charged coupled device (CCD) or complementary metal-oxide semiconductor (CMOS). The light sensor 155 may capture an image of the vessels hidden in the tissue 190. The processor 160 may then analyze the image and identify a location of the vessel. The processor 160 may also utilize the sensed results from the sensor 140 together with the image in identifying the location of the vessels.

In another embodiment, the light source 150 and the light sensor 155 may be installed or incorporated into the instrument 130. For example, the instrument 130 may be a forceps, which has two jaw members. The light source 150 may be installed on one of the two jaw members and the light sensor 155 may be installed on the other of the two jaw members, as described below with reference to FIGS. 2-4 and 9. In yet another embodiment, the light source 150 and the light sensor 155 may both be installed or incorporated into one of the two jaw members as described below with reference to FIG. 5.

Continuing with reference to FIG. 1, when a patient is placed on a surgical table for receiving a surgical operation, an EM wave is generated by an EM wave generator 180. The processor 160 may control the EM wave generator 180 and perform intermittent activation of the EM wave generator 180. The generated EM wave surrounds the patient. An EM sensor 185, which is installed/fixed on the instrument 130 a predetermined distance from its distal tip or other point of reference, senses the strength of the EM wave at the position of the instrument 130. Based on the strength of the EM wave, the processor 160 is able to estimate a location of the instrument 130 with respect to the EM coordinate system. The EM sensor 185 may be installed on another element of the surgical system 100 to monitor the spatial relationship within the surgical system 100. The processor 160 may synchronize the EM coordinate system with the coordinate system of the 3D model.

In embodiments, the EM sensor 185 may have a predetermined spatial relationship with the light source 150 or the light sensor 155. When a location of the vessel is identified based on the sensed results from the light sensor 155, the location of the vessel may be also synchronized with the 3D model and a graphical representation of the vessel may be displayed at the corresponding location in the 3D model in an augmented way. Thus, when the 3D model is moved or rotated, the graphical representation of the vessel is correspondingly moved or rotated.

As an alternative or in addition to incorporating the location of the vessel into the 3D model, a graphical representation of the vessel may be displayed at the corresponding location on a live video image of a surgical site, e.g., a video image obtained from an endoscope and displayed on a surgical display. The graphical representation may be overlaid or projected onto the live video image in an augmented way. In embodiments where video imaging is used, the location of the vessel may be synchronized with the video image, e.g., tissue features, surgical instrument(s), etc. within the video image, such that when the video image is moved or rotated, the graphical representation of the vessel is correspondingly moved or rotated.

After the instrument 130 seals the vessel, the light source 150 emits light to the grasped tissue between the jaw members and the light sensor 155 senses the light, which is the light passing through or reflected from the tissue 190. The processor 160 processes the sensed results from the light sensor 155. The vessel identified after sealing is compared with the vessel identified prior to sealing and/or with sealing parameters. In a case where the dimensions, optical properties, etc. (absolute or relative to the previously identified vessel) of the currently identified vessel indicate that the currently identified vessel has been sufficiently sealed, the processor 160 may confirm that the sealing has been performed completely. Otherwise, the processor 160 determines that the sealing has not been performed completely and informs the clinician to perform sealing again.

In embodiments, where the previously identified vessel is sealed and cut along the seal such that the currently identified vessel includes two sealed vessel portions, the processor 160 may likewise confirm completeness of the sealing of the vessel portions, e.g., based upon dimensions, optical properties, etc. (absolute or relative to the previously identified vessel).

Figure 2:
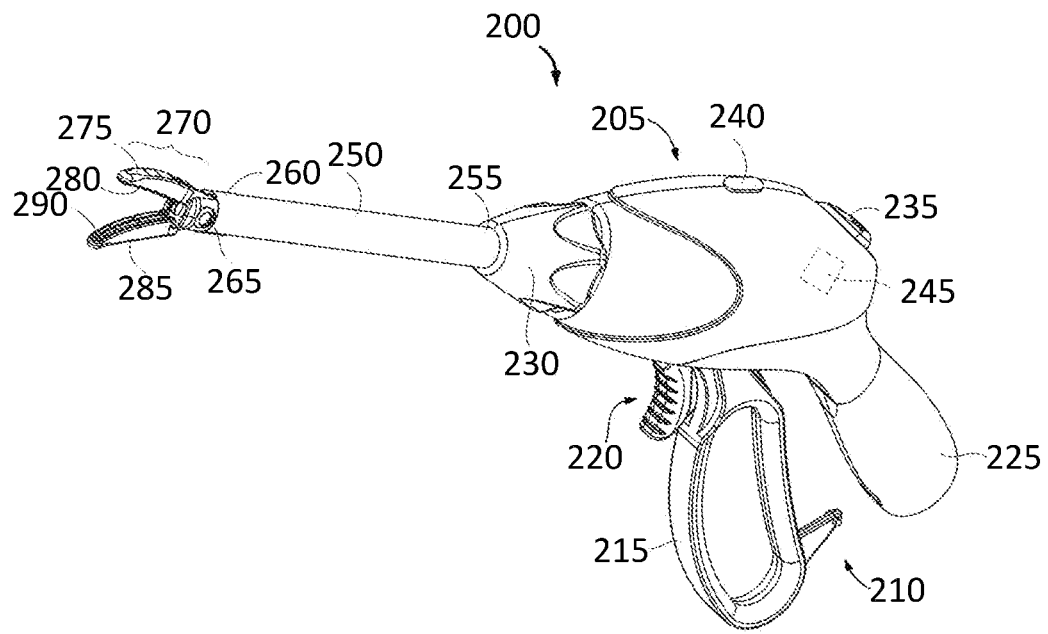
FIG. 2 is a perspective view of an energy-delivery device including an end effector assembly in accordance with aspects of the present disclosure.

FIG. 2 shows a forceps 200 for vessel sealing according to embodiments of the present disclosure. The forceps 200 includes a housing 205, a handle assembly 210, a trigger assembly 220, a rotatable assembly 230, and an end effector assembly 270. The end effector assembly 270 may include any feature or combination of features of jaw members. The components of the forceps 200 are adapted to mutually cooperate to grasp, seal, divide and/or sense tissue, e.g., tubular vessels and vascular tissue. In embodiments, the trigger assembly 220 may be configured to actuate a cutting function, e.g., a knife or electrical cutter, of the forceps 200 or to actuate another component, as described below.

The end effector assembly 270, which is described in various configurations in connection with FIGS. 3A-3B, 4, 5, and 9, generally includes two jaw members 275 and 285 disposed in opposing relation relative to one another. One or both of the jaw members 275 and 285 are movable from a first position wherein the jaw members 275 and 285 are disposed in spaced relation relative to one another to a second position wherein the jaw members 275 and 285 cooperate to grasp tissue therebetween.

The forceps 200 includes an elongated shaft 250 having a distal portion 260 configured to mechanically engage the end effector assembly 270. The proximal portion 255 of the shaft 250 is received within the housing 205. The rotatable assembly 230 is mechanically associated with the shaft 250 such that rotational movement of rotatable assembly 230 imparts similar rotational movements to the shaft 250 that, in turn, rotates the end effector assembly 270.

The handle assembly 210 includes a fixed handle 225 and a movable handle 215. In embodiments, the fixed handle 225 is integrally associated with the housing 205, and the movable handle 215 is selectively movable relative to the fixed handle 225. The movable handle 215 of the handle assembly 210 is ultimately connected to a drive assembly (not shown). As can be appreciated, applying force to move the movable handle 215 toward the fixed handle 225 pulls a drive sleeve of the drive assembly proximally to impart movement to the jaw members 275 and 285 from the first position, wherein the jaw members 275 and 285 are disposed in spaced relation relative to one another, to the second position, where the jaw members 275 and 285 cooperate to grasp tissue located therebetween.

In embodiments, the end effector assembly 270 may be configured as a unilateral assembly that includes a stationary jaw member mounted in fixed relation to the shaft 250 and a pivoting jaw member movably mounted about a pin 265. The jaw members 275 and 285 may be curved at various angles to facilitate manipulation of tissue and/or to provide enhanced line-of-sight for accessing targeted tissues. Alternatively, the forceps 200 may include a bilateral assembly, e.g., both jaw members 275 and 285 move relative to one another and shaft 250.

The forceps 200 further includes first and second switch assemblies 235 and 240 configured to selectively provide energy to the end effector assembly 270. More particularly, the first switch assembly 235 may be configured to perform a first type of surgical procedure (e.g., seal, cut, and/or sense) and a second switch assembly 240 may be configured to perform a second type of surgical procedure (e.g., seal, cut, and/or sense). It should be noted that the presently-disclosed embodiments may include any number of suitable switch assemblies and are not limited to the switch assemblies 235 and 240. It should further be noted that the presently-disclosed embodiments may be configured to perform any suitable surgical procedure and are not limited to only sealing, cutting and sensing. Further, as noted above, cutting may be performed by actuation of the trigger assembly 220, e.g., for mechanical cutting, in addition to or as an alternative to second switch assembly 240.

The forceps 200 may include a controller 245. In embodiments, the controller 245 may be provided as a separate component coupled to the forceps 200 or integrated within the forceps 200. The controller 245 may include any type of computing device, computational circuit, or any type of processor or processing circuit capable of executing a series of instructions that are stored in a memory. The controller 245 may be configured to control one or more operating parameters associated with an energy source (e.g., the power supply 110 or the energy output stage 120 of FIG. 1) based on one or more signals indicative of user input, such as generated by the first and second switch assemblies 235 and 240 and/or one or more separate, user-actuatable buttons or switches. Examples of switch configurations that may be suitable for use with the forceps 200 include, but are not limited to, pushbutton, toggle, rocker, tactile, snap, rotary, slide and thumbwheel. In embodiments, the forceps 200 may be selectively used in either a monopolar mode or a bipolar mode by engagement of the appropriate switch.

The first and second switch assemblies 235 and 240 may also cooperate with the controller 245, which may be configured to automatically trigger one of the switches to change between a first mode (e.g., sealing mode) and a second mode (e.g., cutting mode) upon the detection of one or more parameters or thresholds. In embodiments, the controller 245 is configured to receive feedback information, including various sensor feedback with regard to temperature of tissue, electrical impedance of tissue, jaw closure pressure, jaw positioning, and/or other various feedback information, e.g., using Raman spectroscopy, laser speckle imaging, optical imaging, fluorescence spectroscopy, and/or laser-induced tissue fluorescence, and to control the energy source based on the feedback information.

Embodiments of the present disclosure allow the jaw members 275 and 285 to seal and/or cut tissue using light energy and/or RF energy. In embodiments, the controller 245 may include a feedback loop that indicates when a tissue seal is complete based upon one or more of the following parameters: tissue temperature, light sensing, change in impedance of the tissue over time and/or changes in the optical or electrical power or current applied to the tissue over time, rate of change of these properties and combinations thereof. An audible or visual feedback monitor may be employed to convey information to the surgeon regarding the overall seal quality and/or the completion of an effective tissue seal.

In embodiments, the light source 150 and the light sensor 155 of FIG. 1 may be installed in or fixedly incorporated into one or both of the jaw members 275 and 285 of FIG. 2. When the jaw members 275 and 285 move from the open position to the close position to grasp tissue, the light source 150 emits light or radiates laser to the grasped tissue and the light sensor 155 detects the reflected or scattered light to identify a location of the vessel in the tissue. Details of vessel identification will be described with respect to FIGS. 3A-13 below.

In embodiments, the surgical system 100 may be a robotic surgical system, which includes one or more robotic arms. The forceps 200 may be incorporated into or fixedly installed at one robotic arm with modifications as understood by one of ordinary skilled in the art to adapt a handheld device to one for use with a robotic surgical system.

Figure 3A:
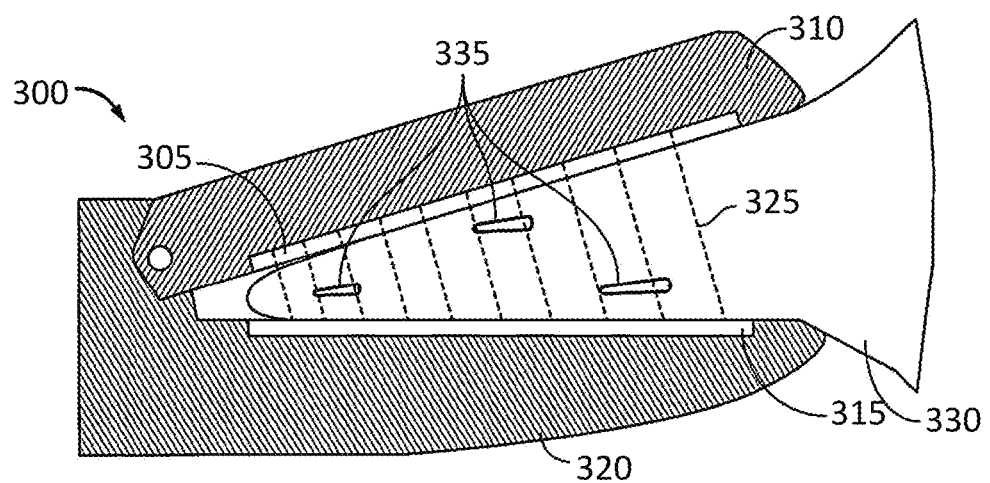
FIGS. 3A and 3B are cross-sectional side views of an end effector assembly of an energy delivery device having jaw members for grasping tissue and blood vessels according to aspects of the present disclosure.
Figure 3B:
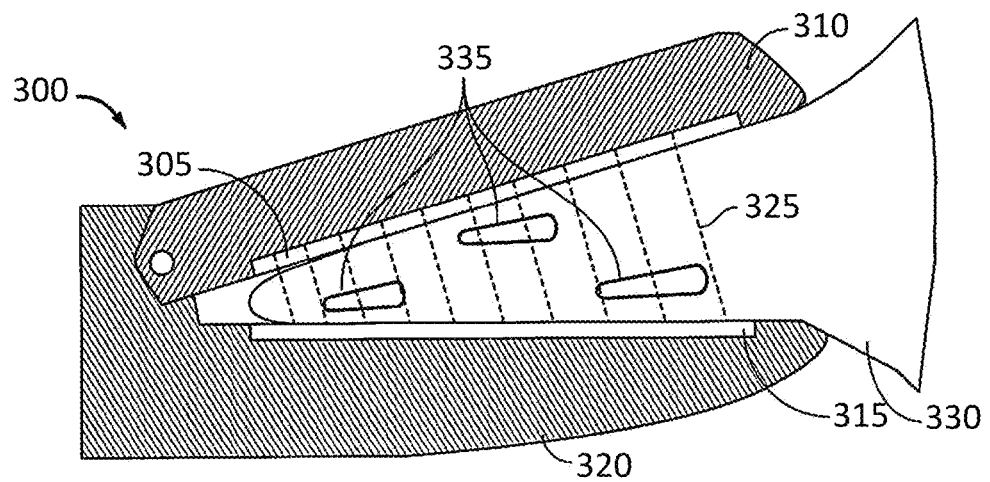

FIGS. 3A and 3B illustrate an energy delivery device 300 including two jaw members 310 and 320, which grasp and compress tissue 330, according to embodiments of the present disclosure. The energy delivery device 300 may be the end effector assembly 270 of FIG. 2. The jaw members 310 and 320 include electrodes 305 and 315 that are electrically coupled to the energy output stage 120 of FIG. 1. The electrodes 305 and 315 receive energy from the energy output stage 120 and apply it to the tissue 330 and vessels 335 within the tissue 330 to perform surgical operations onto the tissue 330 and seal the vessels 335.

As described above, the energy delivery device 300 may be also used in identifying a location of the vessels 335 based on blood circulation in a given volume of tissue 330. To evaluate blood circulation, the given volume of tissue 330 is first grasped between the jaw members 310 and 320 of the energy delivery device 300. The pressure that is applied to the tissue 330 by the jaw members 310 and 320 is selected to provide electrical contacts between the electrodes 305 and 315 and the tissue 330. However, the amount of pressure applied to the tissue 330 may be lower than the amount of pressure used to compress the tissue 330 during tissue sealing. Then, a probing signal 325 (e.g., an RF signal) is applied to the tissue 330 by the electrodes 305 and 315 and a response signal (e.g., tissue impedance) is measured during one or more cardiac cycles.

During the cardiac cycles, the pressure of the blood flowing in the blood vessels 335 varies and, as a result, the relative amount of blood in a given volume of tissue 330 also varies. For example, as shown in FIG. 3A, during a first portion of the cardiac cycle, the pressure of the blood flowing within the blood vessels 335 is at a low level and the volume of blood within the given volume of the tissue 330 is at a low level. On the other hand, as shown in FIG. 3B, during a second portion of the cardiac cycle, the pressure of the blood flowing within the blood vessels 335 is at a high level and the volume of blood within the given volume of tissue 330 is at a high level. The volume of blood within the given volume of tissue 330 may be measured by measuring the impedance of the tissue 330 based on the probing signal 325 to the tissue 330 and sensing the response signal.

During a cardiac cycle, as the volume of blood in a given volume of tissue increases, a force is applied to the jaw members 310 and 320 to urge the jaw members 310 and 320 apart from one another. In embodiments, the surgical system 100 includes a motion sensor configured to sense the change in distance between the jaw members 310 and 320. This distance information may be used together with the response signal 104 to evaluate the level of blood circulation within a given volume of tissue 330.

As described above, a probing signal 325 is applied to the vessels 335 and the response signal is measured over time to identify the tissue 330 and/or the vessels 335 or to determine parameters of the tissue 330 and/or the vessels 335. The response signal may include the frequency and amplitude of an electrical impedance of the tissue 330. If the frequency of the electrical impedance correlates to the frequency of cardiac contractions, then the vessels 335 are identified as a blood vessel. If the vessels 335 are identified as a blood vessel, the amplitude of the electrical impedance would indicate the level of blood circulation.

In embodiments, existence of a blood vessel in the tissue 330 may be determined first based on the response signal from the probing signal 325. In a case when it is determined that the blood vessel exists in the tissue 330, the location of the blood vessel may then be identified, as detailed above. Existence of a blood vessel in the tissue 330 may be also determined by measuring a change in distance or force between the two jaw members 310 and 320.

Figure 4:
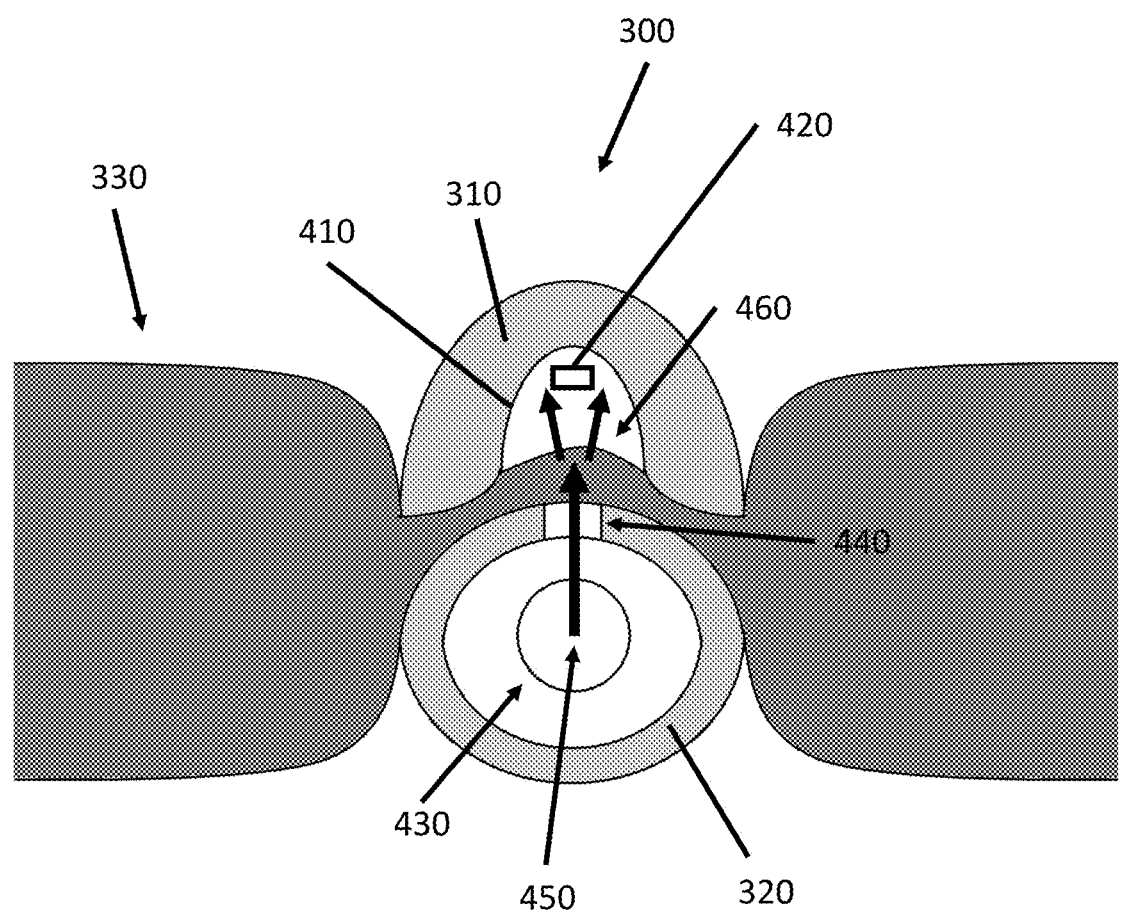
FIG. 4 is a cross-sectional front view of the energy delivery device of FIGS. 3A and 3B for identifying vessels in tissue with an optical light source according to aspects of the present disclosure.

FIG. 4 shows a cross-sectional front view of the energy delivery device 300 of FIGS. 3A and 3B. In this embodiment, jaw members 310 and 320 grasp and deform the tissue 330 by compressing the tissue 330, e.g., extending or stretching the tissue 330 along the length-wise axis of the tissue 330, to intensify the release of elastin and collagen. The upper jaw member 310 includes a cavity 410, in which a light sensor 420 may be positioned. The cavity 410 may be filled with a transparent material so that light can pass through. The bottom portion of the upper jaw member 310 is shaped to mate with the rounded upper portion of the lower jaw member 320, although other configurations are also contemplated such as generally planar jaw surfaces or other complementary jaw configurations.

The lower jaw member 320 includes an optical light source 430 and an aperture 440. The optical light source 430 emits optical light 450, which passes through the tissue 330 via the aperture 440. In an aspect, the lower jaw member 320 may also include a light distribution element (not shown) so that the optical light 450 may be uniformly transmitted to the tissue 330.

In an aspect, the light distribution element may be disposed in the lower jaw member 320 by a predetermined distance from the tissue 330. The light distribution element may include optical fibers, lenses, and/or prisms optically coupled to the light source 430 via a light guide. The optical fibers may contain a grating structure to distribute the optical light 450 out of the side of the optical fibers along a predetermined length of the optical fibers.

As the jaw members 310 and 320 are brought together to deform the tissue 330, the two sides of the upper jaw member 310 stretch or extend the tissue 330, which is to be illuminated by the optical light 450 across the upper portion of the lower jaw member 320. Consequently, the different layers of tissue 330 (e.g., the opposite walls of the vessel 335 of FIGS. 3A and 3B) are made thinner and are brought into contact with each other.

The propagation direction and the wavelength of the optical light 450 are selected to provide the desired tissue penetration depth by the optical light 450. Since neither the light distribution element nor the jaw members 310 and 320 have direct physical contact with the sealed vascular tissue, the sealed vascular tissue never adheres to any portion of the jaw members 310 and 320. In this manner, the jaw members 310 and 320 and the light distribution element avoid contamination by the sealed tissue 330.

When the optical light 450 passes through the grasped tissue 330, the optical light 450 is scattered or dispersed, and the dispersed or scattered light 460 may be sensed by the light sensor 420, which may be a charged coupled device (CCD) or complementary metal-oxide semiconductor (CMOS). The light sensor 420 may capture an image of the vessels hidden in the tissue 330. The processor 160 of FIG. 1 may then analyze the image and identify locations of the vessels.

For example, as described above, the sensed results from the sensor 140 of FIG. 1 may be used to determine whether or not one or more blood vessels exist in the grasped tissue 330. When it is determined that a blood vessel exists within the grasped tissue 330, the optical light source 430 emits the optical light 450 to identify the location of the blood vessel(s) in the grasped tissue 330. The processor 160 may also utilize the sensed results from the sensor 140 of FIG. 1 together with the captured image in identifying the location of the vessels. Further, after sealing the vessel, the light source 430 also emits the optical light 450 so as to confirm whether or not the sealing has been completed.

Figure 5:
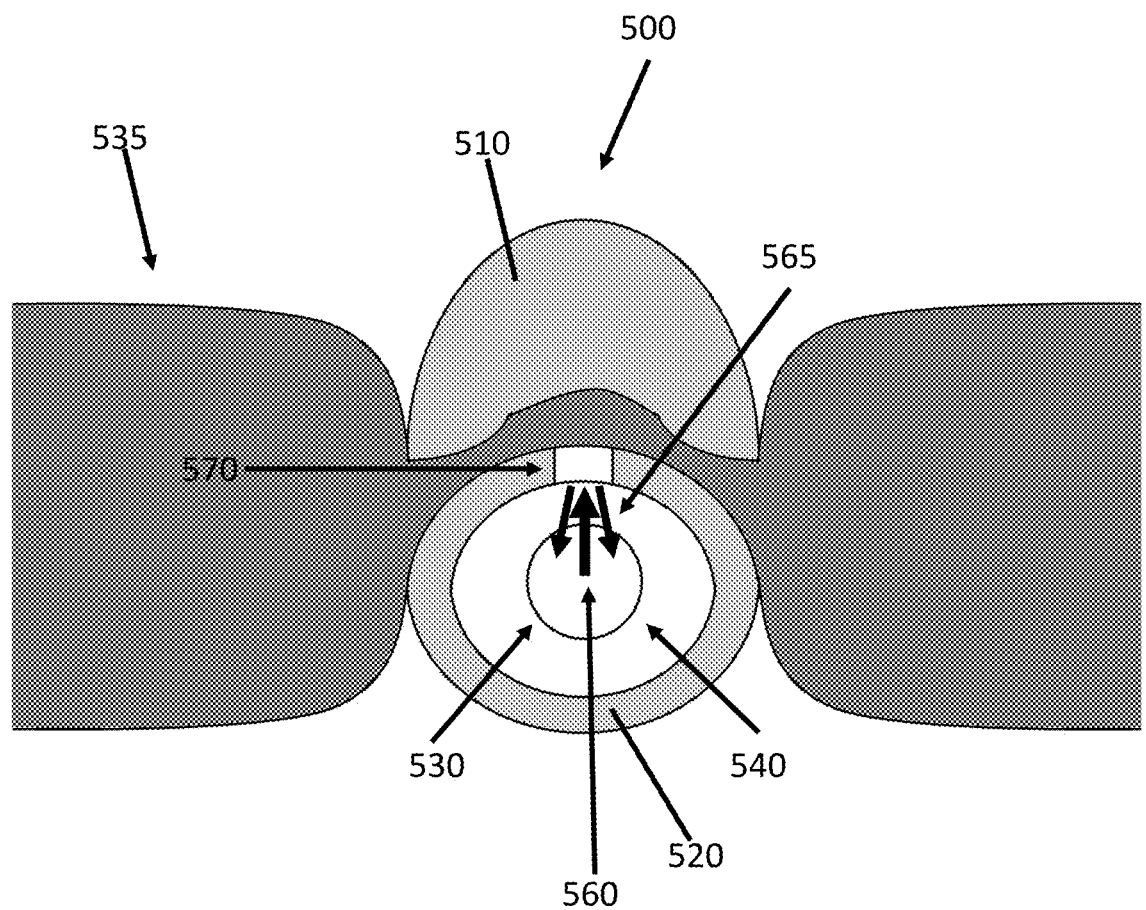
FIG. 5 is a cross-sectional front view of an end effector assembly of an energy delivery device having jaw members for grasping tissue and blood vessels and identifying vessels in tissue with a laser source according to embodiments of the present disclosure.

FIG. 5 illustrates an energy delivery device 500 for identifying a vessel(s) in tissue with a laser source according to embodiments of the present disclosure. The energy delivery device 500 may be of the end effector assembly 270 of the forceps 200 of FIG. 2. Instead of having a light sensor and a light source being fixedly installed on different jaw members as in FIG. 4, a laser source 530 and a light sensor 540 are both fixedly installed in one of two jaw members 510 and 520. As illustrated, the laser source 530 and the light sensor 540 are installed in the lower jaw member 520 but can be in the upper jaw member 510. Alternatively, the light sensor 540 and/or the laser source 530 may be installed in a robotic arm. The laser source 530 irradiates a laser 560, e.g., having a single frequency, into the grasped tissue 535, and the light sensor 540 detects scattered light 565, which has been reflected and scattered from the tissue 535.

The light sensor 540 may be an image sensor such as CCD or CMOS array and may output the sensed results, which may be laser speckle data for processing into laser speckle contrast images (LSCIs). The LSCI allows a clinician to see a quantitative mapping of local blood flow dynamics in a wide area so that the clinician can quickly and accurately assess the blood flows within the tissue 330. Thus, clinicians can see which part of the internal organs have blood vessels supplying blood so that the clinicians may be able to identify a location of blood vessels by looking at the LSCIs in real-time.

Figure 6:
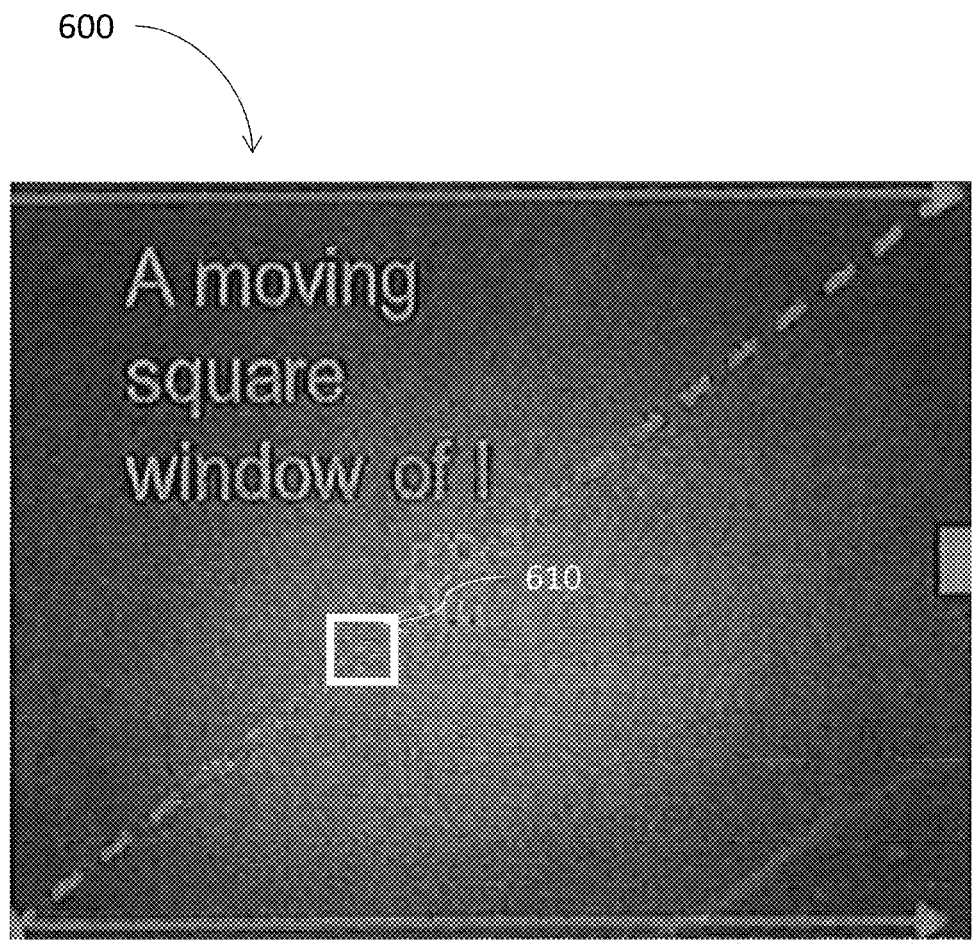
FIG. 6 depicts raw laser speckle data in accordance with aspects of the present disclosure.

FIG. 6 depicts a representation of raw laser speckle data 600 detected from the tissue using a laser, e.g., from laser source 530, which may have one frequency. The light reflected and scattered from the tissue may have different phases and amplitudes, which add together to give a pattern in which its amplitude and intensity vary randomly. Generally, the raw laser speckle pattern has a Gaussian distribution pattern of intensity. Thus, the raw laser speckle data 600 is not readily readable by a clinician and it would be exceedingly difficult to analyze the raw laser speckle data 600 in real time and identify objects in the raw laser speckle data 600. For example, a box 610 is located at a position in the raw laser speckle data 600 where a blood vessel is located. As shown, it is difficult to identify a blood vessel at the box 610 in the raw laser speckle data 600.

When there is a moving object in the area irradiated by the laser source 530, the intensity fluctuates according to the movement of the object (e.g., circulating red blood cells) and thus forms a pattern different from the Gaussian distribution pattern. The laser speckle contrast imaging techniques uses the speckle patterns that are fluctuated by the moving objects or the interference of many waves having the same frequency. By analyzing the intensity fluctuation of these laser speckle patterns together with time, velocity of the moving object can be identified. As a result, the raw laser speckle data 600 of FIG. 6 can be converted to an LSCI of FIGS. 7 and 8 utilizing the following techniques to render an image that is useful to clinicians in practice.

The statistics of noise-like raw laser speckle data 600 is related to speckle contrast K containing a time component. Specifically, the speckle contrast K includes three variables x, y, and t, where x, y, and t represent horizontal, vertical, and temporal position in the sampling space of the laser light. The speckle contrast K(x, y, t) may be defined by a ratio of the standard deviation σ to the mean intensity I as follows:

$$K(x, y, t) = \frac{\sigma(x, y, t)}{\text{AVG}(I(x, y, t))},$$

where σ(x, y, t) is the standard deviation of intensity in spatial and time domain, I(x, y, t) is the intensity values of a set of pixels adjacent to position (x, y, t) in spatial and time domain, and AVG(I(x,y,t)) is the mean or average intensity of the set of pixels adjacent to the position (x, y, t). In embodiments, the set of pixels may be defined by a time series of intensity of an individual pixel, pixels in a rectangular window in the (x, y) plane at time t, or a consecutive cubic in the (x, y, t) space.

The depth of modulation of the speckle intensity fluctuations generally gives some indication of how much of the laser light is being scattered from moving objects and how much from stationary objects. Further, the frequency spectrum of the fluctuations depends on velocity distribution of the movements of the moving objects. It follows that the speckle contrast K is related to velocity of moving objects or simply subsurface blood flows here. The speckle contrast K is then expressed as the following equation:

$$K = \left[\frac{\tau_c}{2T}\left(1 - e^{\left(\frac{-2T}{\tau_c}\right)}\right)\right]^{\frac{1}{2}},$$

where T is an integration time and $\tau_c$ is a correlation time. Velocity V is a reciprocal of the correlation time $\tau_c$. Thus, the speckle contrast K becomes:

$$K = \left[\frac{1}{2TV}\left(1 - e^{-2TV}\right)\right]^{\frac{1}{2}}.$$

According to this equation, when the velocity V increases, the exponential term $e^{-2TV}$ is going to be closer to zero and the speckle contrast K is going to increase to a value which is less than $$\sqrt{\frac{1}{2TV}}.$$

Since the velocity V is assumed to be greater than or equal to zero, the speckle contrast K is greater than or equal to zero, and bound by $$\sqrt{\frac{1}{2TV}}.$$

Based on the equation of the speckle contrast K and the velocity, the squared value of the speckle contrast K is inversely proportional to the velocity V, when assuming that the exponential term $e^{-2TV}$ is comparatively small. Or, in other words, the value $$\frac{1}{K^2}$$

is linearly proportional to the velocity V.

The processor 160 of the surgical system 100 (FIG. 1) normalizes the value $$\frac{1}{K^2(x, y, t)}$$

and converts the normalized value into intensity of a pixel (x, y) of the laser speckle contrast image. Since $$\frac{1}{K^2(x, y, t)}$$

is inversely proportional to the velocity V, if $$\frac{1}{K^2(x, y, t)}$$

is small, the velocity is also small and intensity of the pixel (x, y) is low and, if $$\frac{1}{K^2(x, y, t)}$$

is large, the velocity V is correspondingly large and the intensity of the pixel (x, y) is high. Thus, a portion of a vessel where the blood flows slowly is illustrated darker than a portion of a vessel where the blood flows faster. However, the way of converting laser speckle into intensity is not limited by the equation presented above as the above is provided as an example. Any correlation between the laser speckle and intensity can be made within the scope of this disclosure by a person having ordinary skill in this art.

Further, the intensities of pixels resulted from the LSCI processes may be normalized, formatted for display, stored, and passed to other processes such as noise reduction, pseudo color rendering, or fusion with white light image, etc.

Figure 7:
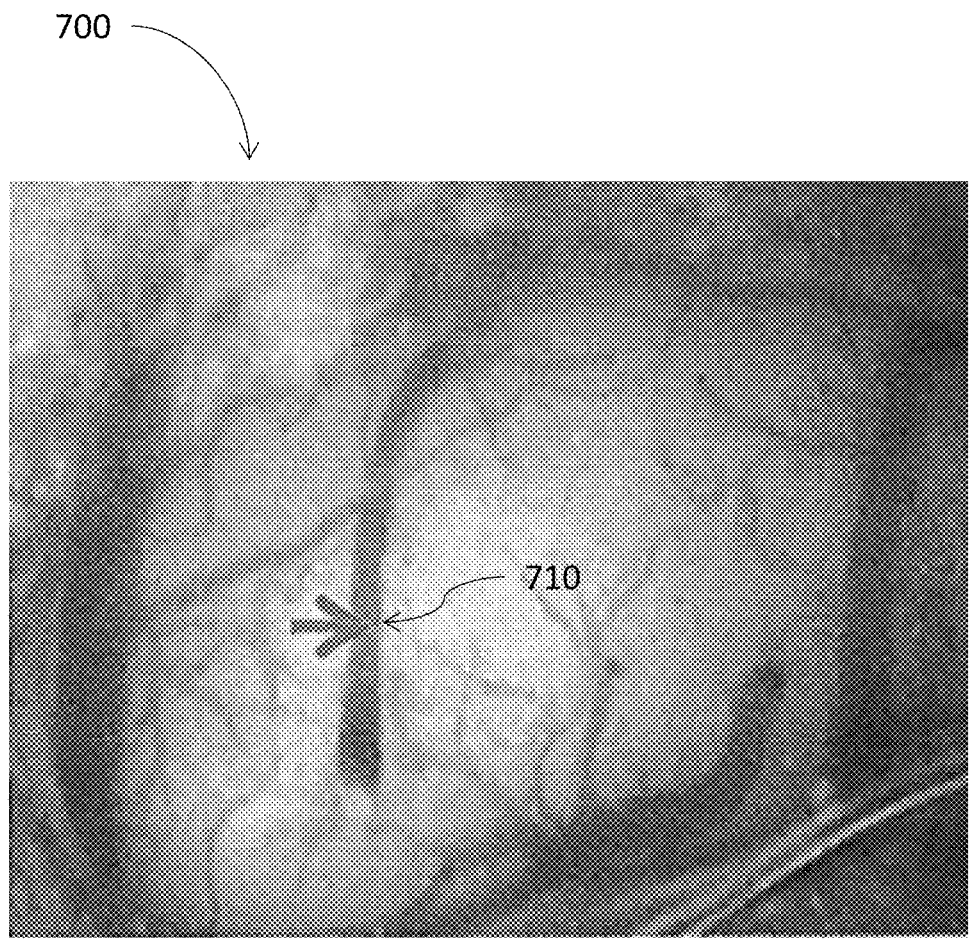
FIG. 7 is a laser speckle contrast image (LSCI) illustrating subsurface blood flows in tissue obtained based on laser speckle data prior to vessel sealing according to aspects of the present disclosure.

The optical image 700 of FIG. 7 may be generated by an optical light sensor (e.g., the light sensor 420 of FIG. 4) prior to vessel sealing and prior to clamping of the tissue. The location 710 of FIG. 7 corresponds to the location of the box 610 of FIG. 6. The optical image 700 is readily usable by a clinician to see blood vessels in the whole view of the image and to identify a location of the vessel at the location 710, while the box 610 of the raw laser speckle data 600 of FIG.

6 does not show legible vessels. The optical image 700 may be overlaid on an image from other modalities or displayed over another image in a manner of augmented reality Based on the optical image 700, clinicians may seal the identified vessel prior to or concurrently with a surgical operation. The optical image 700 shows there are a blood vessel and probably a blood flow at the location 710.

Figure 8:
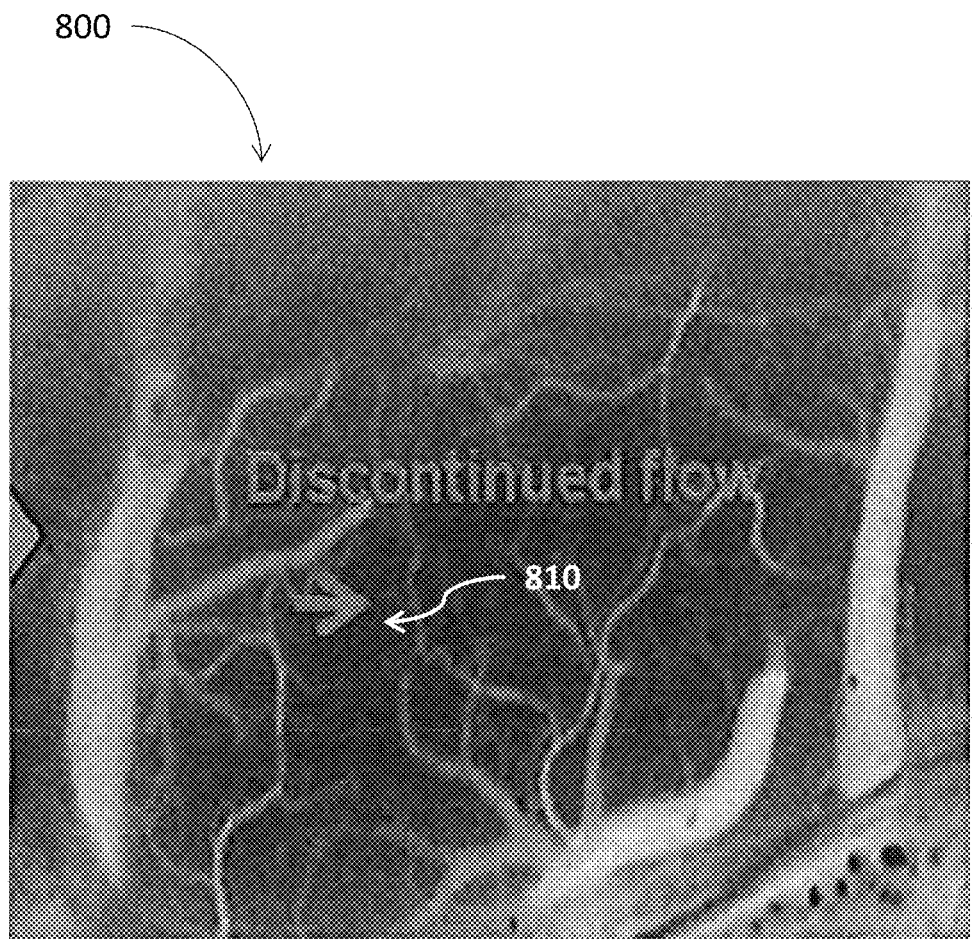
FIG. 8 is an LSCI illustrating subsurface blood flows of the same portion of the tissue as FIG. 7 after vessel sealing.

FIG. 8 shows an LSCI 800 after sealing the vessel. The location 810 corresponds to the location of the box 610 of FIG. 6 and the location 710 of FIG. 7. As shown, there is no blood flow at the location 810, meaning that the blood vessel at the location 810 has no blood flow and thus has been sealed completely. Thus, by comparing an LSCI, which has been obtained prior to vessel sealing, with the LSCI 800, which has been obtained after the vessel sealing, the surgical system may be able to confirm that vessel sealing has been completed.

Figure 9:
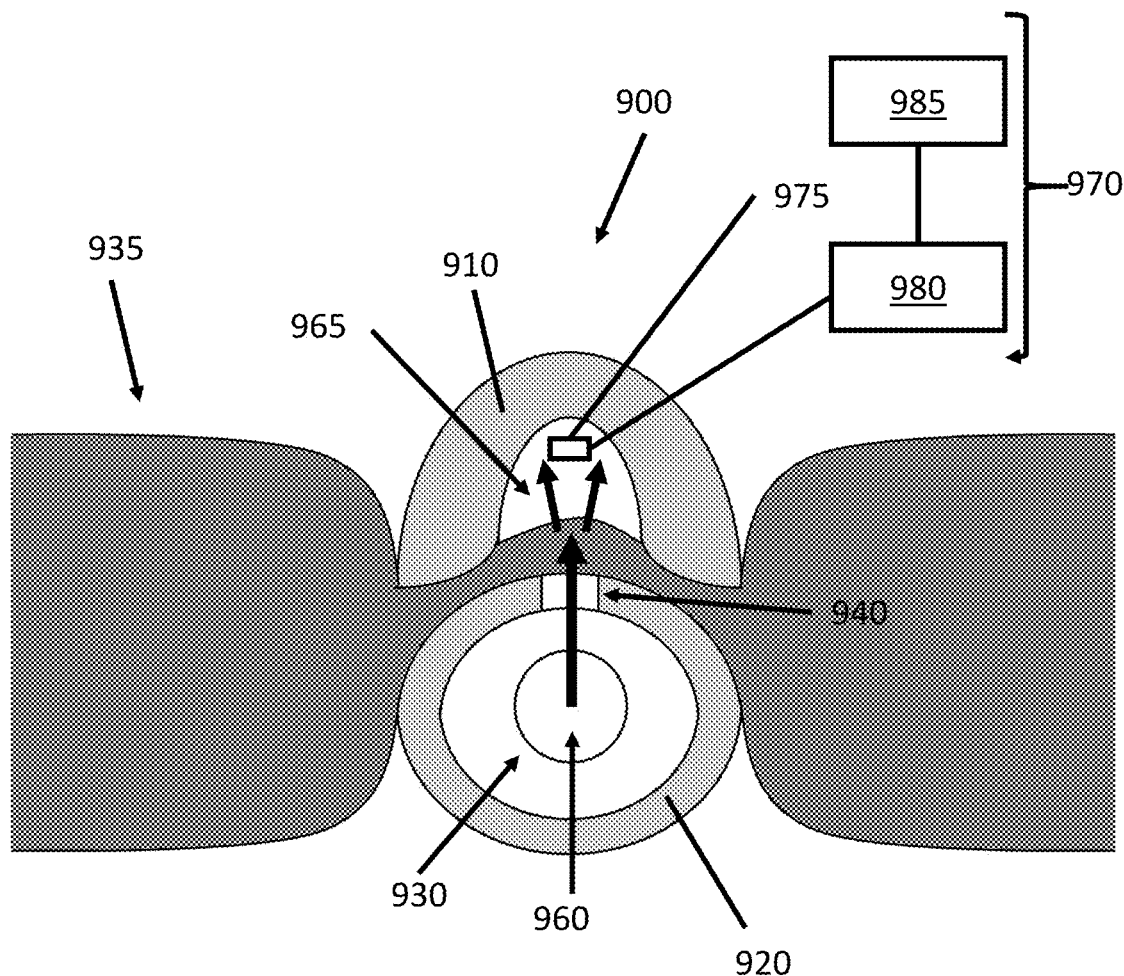
FIG. 9 is a cross-sectional front view of an end effector assembly of an energy delivery device having jaw members for grasping tissue and blood vessels and identifying vessels in tissue with a laser source based on Raman Shift according to aspects of the present disclosure.

In embodiments, identification of the locations of vessels and confirmation of vessel sealing may be performed based on Raman spectroscopy, which enables rapidly capturing the molecular environment of tissues without destroying or altering the tissues. FIG. 9 illustrates an energy delivery device 900 for identifying vessel in tissue based on Raman shifts. The energy delivery device 900 includes first and second jaw members 910 and 920 configured to grasp tissue 935. The second jaw member 920 includes a laser source 930 having at least one frequency and the first jaw member 910 includes a light sensor 970.

The laser source 930 irradiates a laser light 960 onto the grasped tissue 935. The laser light 960 may include a laser having a frequency of 375 nm and/or 405 nm. When the laser light 960 passes through the grasped tissue 935, it is scattered. The light sensor 970 then detects or senses the scattered light 965. The light sensor 970 may include a microscope 975, a spectroscope 980, and a detector 985. The microscope 975 may be able to extract information in a minute area less than or equal to 1 µm with a help of a filter. The spectroscope 980 may incorporate an appropriate diffraction grating to obtain a corresponding spectral resolution so that the detector 985 may be able to detect a Raman shift.

Raman spectroscopy generates information-rich spectra that, when combined with chemometrics, provide powerful insight into the molecular diversity within tissue. For example, information regarding amino acids (e.g., amide bonds between amino acids and their tertiary structure) can be extracted and analyzed based on the Raman spectroscopy.

When a laser light 960 is irradiated on tissue by the laser source 930, photons are absorbed and scattered by the tissue 935. The Raman effect arises when an energy incident to the tissue 935 is different from an energy scattered by the tissue 935. Different constituents have different Raman effects. With this difference, a photonic energy shift occurs in the scattered light 965. For example, when the incident energy is larger than the scattered energy, Stokes scatter occurs, and when the incident energy is smaller than the scattered energy, anti-Stokes scatter occurs. Since the energy shift is small, Raman shift is calculated by subtracting a reciprocal of the wavelength scattered from a reciprocal of the wavelength incident, namely:

$$v = \frac{1}{\lambda_{incident}} - \frac{1}{\lambda_{scattered}},$$

where $v$ is a Raman shift in wave number, $\lambda_{incident}$ is a wavelength of the light incident to the tissue, and $\lambda_{scattered}$ is a wavelength of the light scattered by the tissue. Thus, the wave number of the Raman shift has a unit of $$\frac{1}{distance}$$

or $cm^{-1}$.

For example, Raman bands corresponding to C—C stretch of proline (855 $cm^{-1}$), C—C stretch of hydroxyproline (874 $cm^{-1}$), C—N stretch of proline (919 $cm^{-1}$), proline (1043 $cm^{-1}$), and Amide 3 (1245-1270 $cm^{-1}$) are notable. The hydroxyproline and two proline peaks are specifically Raman collagen assignments confirming a collagen presence. Non-collagen rich tissue indicative of biological tissue includes bands corresponding to cholesterols (699 $cm^{-1}$), phenlalanine (1003 $cm^{-1}$), C—H deformation of proteins (1262 $cm^{-1}$) and carbohydrates (1342 $cm^{-1}$), amide II (1480 $cm^{-1}$), and amide I (1663 $cm^{-1}$).

For exemplary purposes only, spectra showing an abundance value greater than 0.6 of a collagen rich end-member were selected and the mean of these spectra was then calculated for each graph. These means were then compared between healthy and sealed areas to identify changes in the collagen environment due to sealing via a difference spectrum. Sealed porcine blood vessel tissue, for example, have shown changes in the 1252-1261 $cm^{-1}$ peaks and a shift to lower wave-numbers in the 1447 $cm^{-1}$ peak. The 1600-1650 $cm^{-1}$ Amide 1 band showed a shift to higher wave-numbers. For bowel tissues, only the samples which were sealed with no compression and at 0.2 mega pascal (MPa) compression were used for comparison as these sample maps included more than 3 spectra which met the threshold requirements. The changes in the collagen rich spectra between sealed and healthy areas were less pronounced in the porcine bowel tissue samples when compared to sealed blood vessels. In comparison to sealed blood vessels, bowel tissue sealed at 0.2 MPa compression pressure demonstrated similar trends in the protein band shifts, specifically in the three broad protein bands, 1245-1270, 1445, and 1665 $cm^{-1}$, corresponding to the Amide 3, $CH_2$ bending, and Amide 1 bands, respectively, though less distinct. In bowel tissue sealed without compression, band shift trends included the 1245 and 1665 $cm^{-1}$ Amide 3 and Amide 1 band, respectively; however, less dramatic shifts were seen in other protein bands (FIGS. 10A-10C).

Figure 10A:
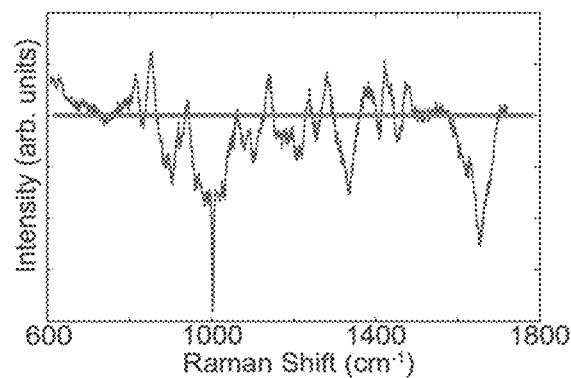
FIGS. 10A-10C are graphical representations of Raman Shifts according to aspects of the present disclosure.
Figure 10B:
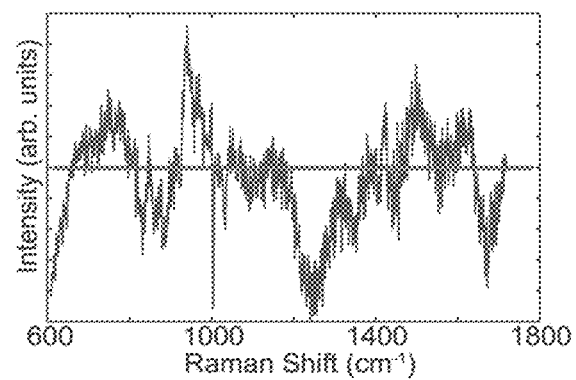
Figure 10C:
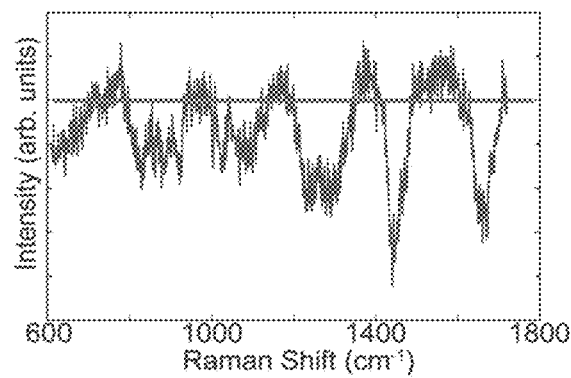

Referring to FIGS. 10A-10C, Raman spectra are shown of healthy, RF-sealed collagen rich tissue areas from RF sealed porcine blood vessel (FIG. 10A), RF-sealed porcine bowel tissue without compression (FIG. 10B), and at 0.20 MPa compression pressure (FIG. 10C). The 1313 $cm^{-1}$, 1324 $cm^{-1}$, 1252-1261 $cm^{-1}$ and 1600-1690 $cm^{-1}$ peaks are highlighted corresponding to the $CH_3CH_2$ twisting and wagging mode of collagen, respectively; Amide 3 and Amide 1 (nonreducible collagen crosslinks at lower wavenumbers and reducible collagen crosslinks at higher wavenumbers) respectively.

For thermal denaturing of collagen, the 1660 $cm^{-1}$ band is shifted to higher wave-numbers in the sealed tissue area, thereby suggesting an increase in reducible crosslinks and a decrease of non-reducible cross links within the collagen. Additionally, a shift in the 1302 $cm^{-1}$ peak to higher wave-numbers has been identified in collagen thermal denaturing. Changes in the 1313 $cm^{-1}$ and 1324 $cm^{-1}$ peaks signifying changes in the $CH_3CH_2$ twisting and wagging modes of collagen also demonstrated a disruption to the native collagen. Lastly, the apparent shift of the 1252-1261 $cm^{-1}$ peaks to lower frequencies also implicate crosslinks may have been reduced or broken. RF sealing of the porcine bowel tissue demonstrated less pronounced differences; however, sealing performed at 0.2 MPa compression pressure demonstrated many of the same changes, including shifts in the 1252-1261, 1313, 1324, 1443, and 1660 $cm^{-1}$ bands, seen in the sealed blood vessels, again indicating a denaturing of collagen and, more specifically, a decrease in non-reducible cross links and an increase in reducible cross links as seen in FIG. 10C.

This molecular restructuring appears to be less collagen dependent as shown in the Raman difference plots in FIG. 10B with collagen difference spectrum highlighting fewer distinct band shifts in compressed tissue versus non-compressed tissue. This may be attributed to more collagen bond restructuring with the additional mechanical pressure during sealing introduced with tissue compression.

As described above, the blood vessel has its own characteristics in frequency shifts (i.e., Raman shifts) based on molecular bonds (e.g., $CH_2$ bond, amino bond, etc.) and structure (e.g., $CH_3CH_2$ twist and wagging mode of collagen). When the blood vessel is sealed, its molecular bonds and structure are changed, thereby changing characteristics of the Raman shifts. Thus, based on frequency shifts in Raman spectroscopy, blood vessels may be identified and sealing of the blood vessels can be confirmed in vitro. Further, the Raman spectra may identify strong or weak seal by conducting Raman spectroscopy over the sealing area.

By finding a Raman shift, which is only identified in blood vessels, the same can be identified and, by finding another Raman shift, which can be found only in sealed vessels, sealing of the vessels can be confirmed.

Figure 11:
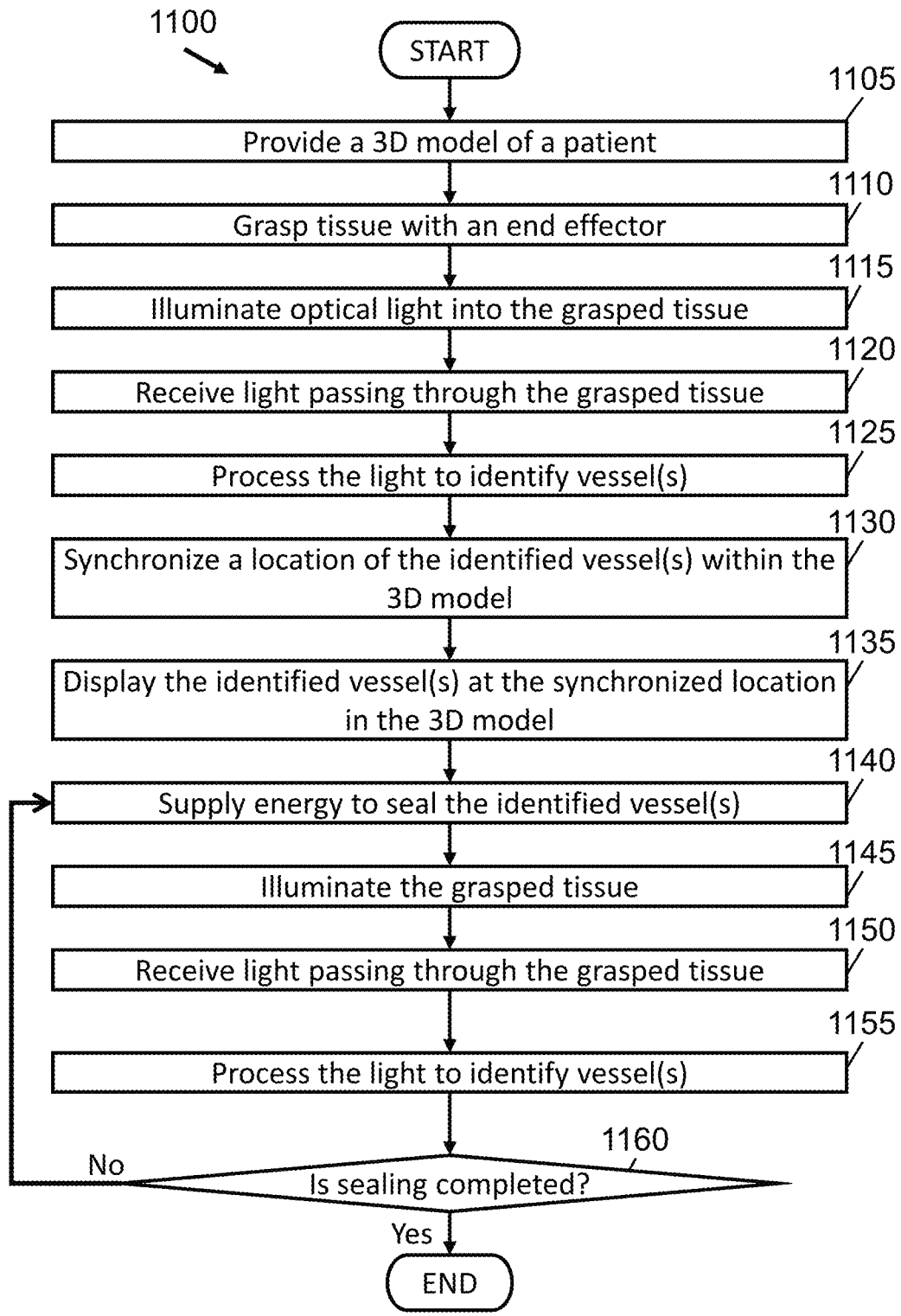
FIG. 11 is a flowchart illustrating a method for identifying blood vessels based on optical light according to aspects of the present disclosure.

FIG. 11 shows a flowchart illustrating a method 1100 for identifying blood vessels and confirming sealing of blood vessels based on optical light. The method 1100 starts by providing to a surgical system a 3D model of a patient in step 1105. The 3D model may include a region of interest in the patient based on CT image data or other image data in the DICOM format. In an embodiment, a live video may be provided to show anatomical structures or the 3D model may be generated from a live video. The surgical system may include EM tracking sensors fixedly or slidably installed on an end effector having two jaw members.

In step 1110, the end effector grasps tissue of interest with two jaw members. One jaw member may include an optical light source and the other jaw member may include a light sensor. In step 1115, the optical light source illuminates an optical light to the tissue. When the optical light passes through the tissue, the light is scattered and the light sensor receives the light, which has passed through and been scattered by the grasped tissue in step 1120. The light sensor may be a CCD or CMOS and generate an image based on the received light.

In step 1125, the received light is processed to identify blood vessel(s). In an aspect, the generated image may be processed to identify the blood vessel(s).

As described above, an EM tracking sensor is installed on one of the two jaw members such that the location of the optical light source or the light sensor may be estimated by the EM tracking sensor. Further, in consideration of the estimated location, the location of the identified blood vessel(s) may be identified. In step 1130, the location of the identified blood vessel(s) may be synchronized with the 3D model. In other words, the location of the identified blood vessel in the real world is mapped to the 3D model of the patient, so that the corresponding location of the identified blood vessel in the 3D model can be calculated.

In step 1135, the identified blood vessel(s) is displayed, as a graphical representation, at the calculated location with respect to the 3D model on a display. Thus, the clinicians performing a surgical operation may be able to locate a surgical device at a proper position based on the synchronized location of the identified blood vessel(s) as displayed in the display.

After positioning the surgical device at the proper location, surgical energy may be supplied to the tissue via the surgical device to seal the identified blood vessel(s) in step 1340. In an aspect, the surgical energy may be RF, microwave, or electromagnetic energy.

After sealing the tissue, proper sealing of the identified vessel(s) can be confirmed. In this regard, the grasped tissue is illuminated again by the optical light source in step 1145. Then, the light sensor again receives the light, which has passed through and been scattered by the grasped tissue in step 1150.

In step 1155, the received light is processed to identify vessel(s), which corresponds to the identified vessel in step 1125.

In step 1160, it is determined whether or not the identified vessel(s) has been sealed completely. As described above in step 1125, the received light may be used to generate an image. In this regard, prior to sealing, a first image may be generated and, after sealing, a second image may be generated. Based on image processing, a vessel may be identified in the first and second images. The identified vessel in the first image is then compared with the corresponding vessel in the second image. In a case when the dimensions, optical properties, etc. (absolute or relative to the previously identified vessel) of the currently identified vessel indicate that the currently identified vessel has been sufficiently sealed, the sealing of the identified vessel is confirmed.

Image processing is not limited to the above-described ways but may be performed in other ways, which are readily appreciated by a person having ordinary skill in the art, to confirm completeness of sealing of the identified vessel.

When it is not confirmed that the identified vessel has been completely sealed, the method 1100 goes to step 1140 to further perform sealing of the identified vessel. When the sealing is confirmed in step 1160, the method 1100 is ended.

Figure 12:
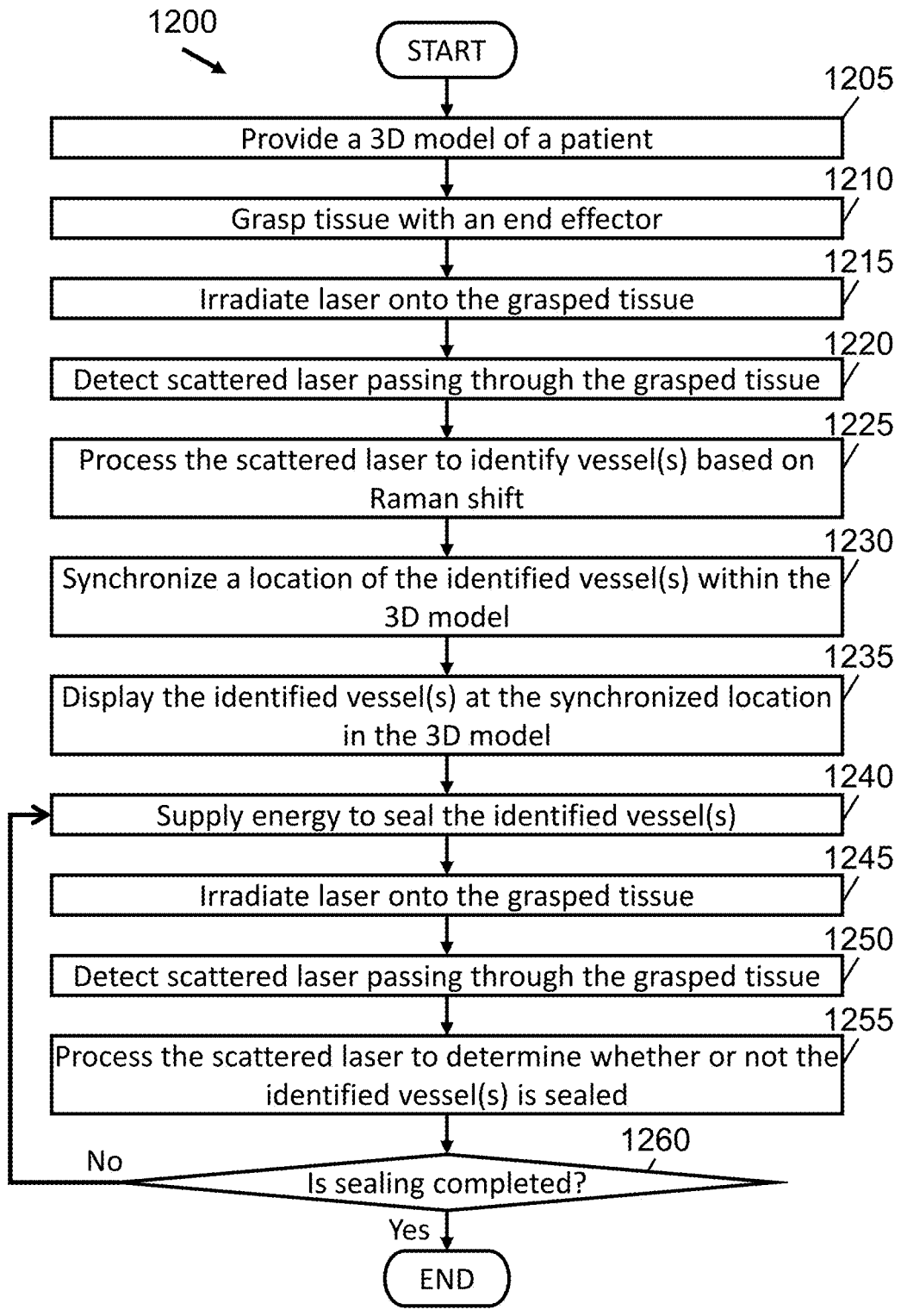
FIG. 12 is a flowchart illustrating a method for identifying blood vessels based on Raman shifts according to aspects of the present disclosure.

FIG. 12 shows a flowchart illustrating a method for identifying blood vessel(s) based on Raman shifts. The method 1200 starts by providing to a surgical system a 3D model of a patient in step 1205. In an embodiment, a live video may be provided to show anatomical structures or the 3D model may be generated from a live video. The 3D model may include a region of interest in the patient based on CT image data or other image data in the DICOM format. The surgical system may include EM tracking sensors fixedly or slidably installed on one of two jaw members of an end effector.

In step 1210, the end effector grasps tissue of interest with the two jaw members. A laser source is installed on one of the two jaw members and a light sensor is installed on the other one of the two jaw members. In step 1215, the laser source irradiates a laser light, which may include one or more frequencies, to the grasped tissue. When the laser light is irradiated into the grasped tissue, the laser light is scattered while passing through the grasped tissue. The scattered laser light is detected by the light sensor in step 1220.

The scattered laser light includes frequency shift data, which is Raman shifts. When there is a difference between received energy and emitting energy by the grasped tissue, such the difference is expressed in frequency shifts. Further, when molecular structure or composition is changed, the frequency shift also changes. That is, the Raman shift, the received scattered laser is processed to identify blood vessel(s) in step 1225. Since the blood vessel(s) has a specific frequency shift different from the other tissue elements, the blood vessel(s) can be identified by combining areas where the specific frequency shift is detected.

As described above, an EM tracking sensor is installed either one of the two jaw members. As described in step 1230 of FIG. 12, the location of the identified blood vessel(s) may be synchronized with the 3D model in step 1230.

In step 1235, the location of the identified blood vessel(s) is displayed on a display with respect to the 3D model. Thus, the clinicians performing a surgical operation may be able to locate a surgical device at a proper position based on the synchronized location of the identified blood vessel(s) as displayed in the display.

After positioning the surgical device at the proper location, surgical energy may be supplied to the tissue via the surgical device to seal the identified blood vessel(s) in step 1240. In an aspect, the surgical energy may be RF, microwave, or electromagnetic energy.

After sealing the tissue, it is necessary to confirm that the identified vessel(s) has been sealed properly prior to or concurrently with further treatment to the tissue. In this regard, the laser source irradiates the laser light again onto the grasped tissue in step 1245. Then, the light sensor again detects the scattered light, which has passed through the grasped tissue and has been scattered by the grasped tissue in step 1250.

In step 1255, the detected scattered laser is processed to identify vessel(s), which corresponds to the identified vessel(s) in step 1225.

In step 1260, it is determined whether or not the identified vessel(s) has been sealed completely. As described above in step 1225, the detected laser may be processed to generate an image. In this regard, prior to sealing, a first image may be generated and, after sealing, a second image may be generated. Based on image processing, a vessel may be identified in the first and second images. The identified vessel in the first image is then compared with the corresponding identified vessel in the second image. In a case when the dimensions, optical properties, etc. (absolute or relative to the previously identified vessel) of the currently identified vessel indicate that the currently identified vessel has been sufficiently sealed, the sealing of the identified vessel is confirmed.

Image processing is not limited to the above-described ways but may be performed in other ways, which are readily appreciated by a person having ordinary skill in the art, to confirm completeness of sealing of the identified vessel.

When it is not confirmed that the identified vessel has been completely sealed, the method 1200 goes to step 1240 to further perform sealing of the identified vessel. When the sealing is confirmed in step 1260, the method 1200 is ended.

Figure 13:
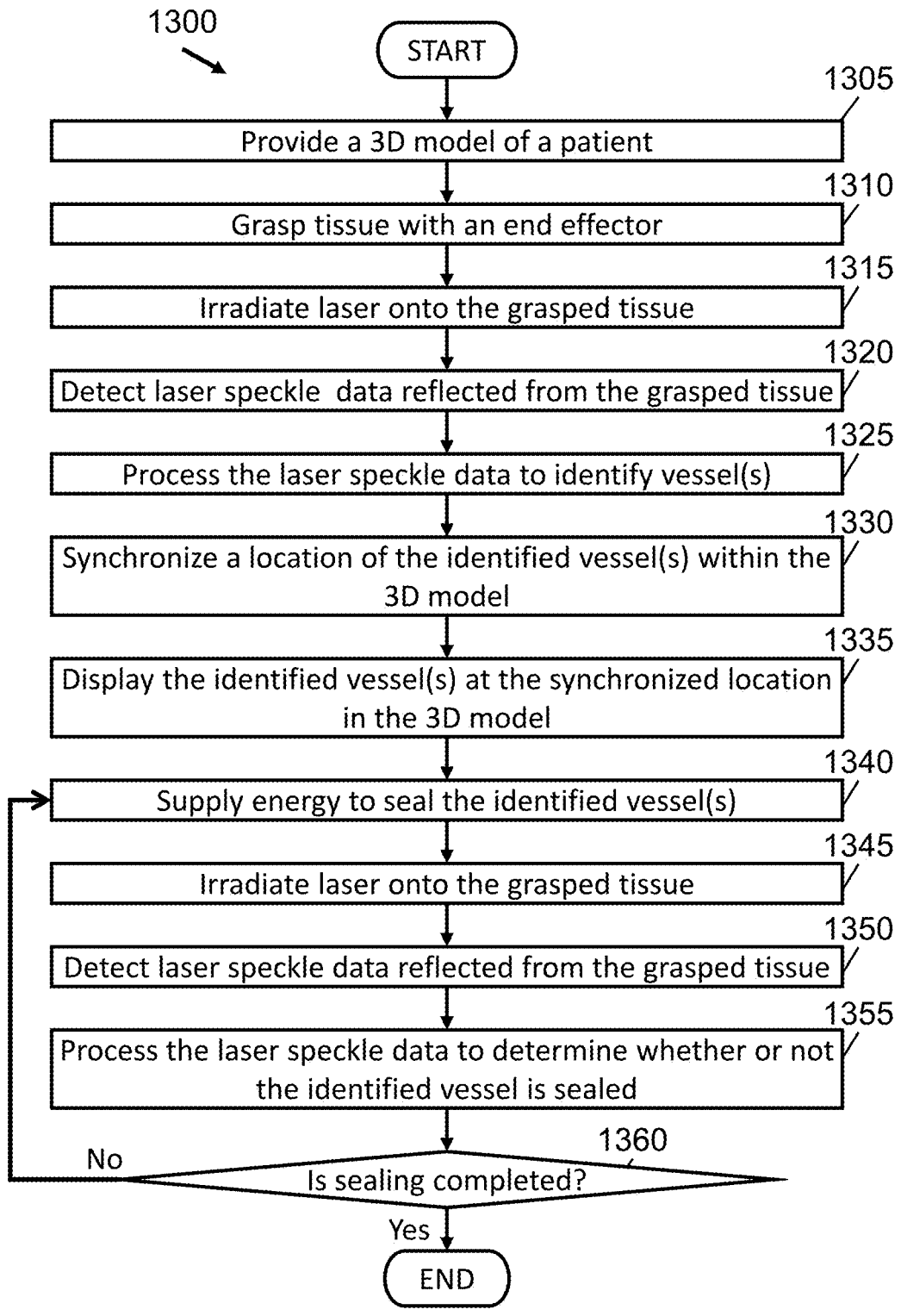
FIG. 13 is a flowchart illustrating a method for identifying blood vessels based on laser speckle data according to aspects of the present disclosure.

FIG. 13 shows a flowchart illustrating a method 1300 for identifying blood vessel(s) and confirming sealing of blood vessel(s) based on laser speckle data. The method 1300 starts by providing to a surgical system a 3D model of a patient in step 1305. In an embodiment, a live video may be provided to show anatomical structures or the 3D model may be generated from a live video. The 3D model may include a region of interest in the patient based on CT image data or other image data in the DICOM format. The surgical system may include EM tracking sensors fixedly or slidably installed on one of two jaw members of an end effector.

In step 1310, the end effector grasps tissue of interest with the two jaw members. A laser source and a light sensor are installed on only one of the two jaw members. In step 1315, the laser source irradiates a laser light, which includes only one frequency, to the grasped tissue. When the laser light is irradiated into the grasped tissue, the laser light is scattered and reflected off from the surface of the grasped tissue. The scattered laser light is detected by the light sensor in step 1320.

The scattered laser light includes laser speckle data, which includes intensity fluctuation data. When there is a moving object in the area irradiated by the laser source, the intensity fluctuates according to the movement of the moving object (e.g., circulating red blood cells) and thus forms a pattern different from the Gaussian distribution pattern. By analyzing the intensity fluctuation of these laser speckle patterns together with time, velocity of the moving object can be identified. Based on the velocity of the red blood cells, a blood vessel may be identified. In this way, the laser speckle data is processed to identify blood vessel(s) based on the laser speckle data or patterns in step 1325.

As described in step 1230 of FIG. 12, the location of the identified blood vessel(s) may be synchronized with the 3D model in step 1330.

As described above, an EM tracking sensor is installed the one jaw member, where the laser light source and the light sensor are installed. In step 1335, the location of the identified blood vessel(s) is displayed on a display with respect to the 3D model. Thus, the clinicians performing a surgical operation may be able to locate a surgical device at a proper position based on the synchronized location of the identified blood vessel as displayed in the display.

After positioning the surgical device at the proper location, surgical energy may be supplied to the tissue via the surgical device to seal the identified blood vessel(s) in step 1340. In an aspect, the surgical energy may be RF, microwave, or electromagnetic energy.

After sealing the tissue, it is confirmed that the identified vessel has been sealed properly prior to or concurrently with further treatment to the tissue. In this regard, the laser source irradiates the laser light again onto the grasped tissue in step 1345. Then, the light sensor again detects the light, as laser speckle data, which is scattered and reflected off from the surface of the grasped tissue in step 1350.

In step 1355, the received laser speckle data is processed to identify vessel(s), which corresponds to the identified vessel(s) in step 1325.

In step 1360, it is determined whether or not the identified vessel(s) has been sealed completely. As described above in step 1325, the detected laser speckle data may be processed to generate an image including intensity corresponding to movements of the red blood cells. In this regard, prior to sealing, a first image may be generated and, after sealing, a second image may be generated. Based on image processing, a vessel may be identified in the first and second images. The identified vessel in the first image is then compared with the corresponding identified vessel in the second image. In a case when the dimensions, optical properties, etc. (absolute or relative to the previously identified vessel) of the currently identified vessel indicate that the currently identified vessel has been sufficiently sealed, the sealing of the identified vessel is confirmed.

Image processing is not limited to the above-described ways but may be performed in other ways, which are readily appreciated by a person having ordinary skill in the art, to confirm completeness of sealing of the identified vessel. For example, ultrasound imaging modality may be used to detect a flow rate before, during, and after the sealing and to confirm completion of the sealing.

When it is not confirmed that the identified vessel has been completely sealed, the method 1300 goes to step 1340 to further perform sealing of the identified vessel. When sealing is confirmed in step 1360, the method 1300 is ended.

Figure 14:
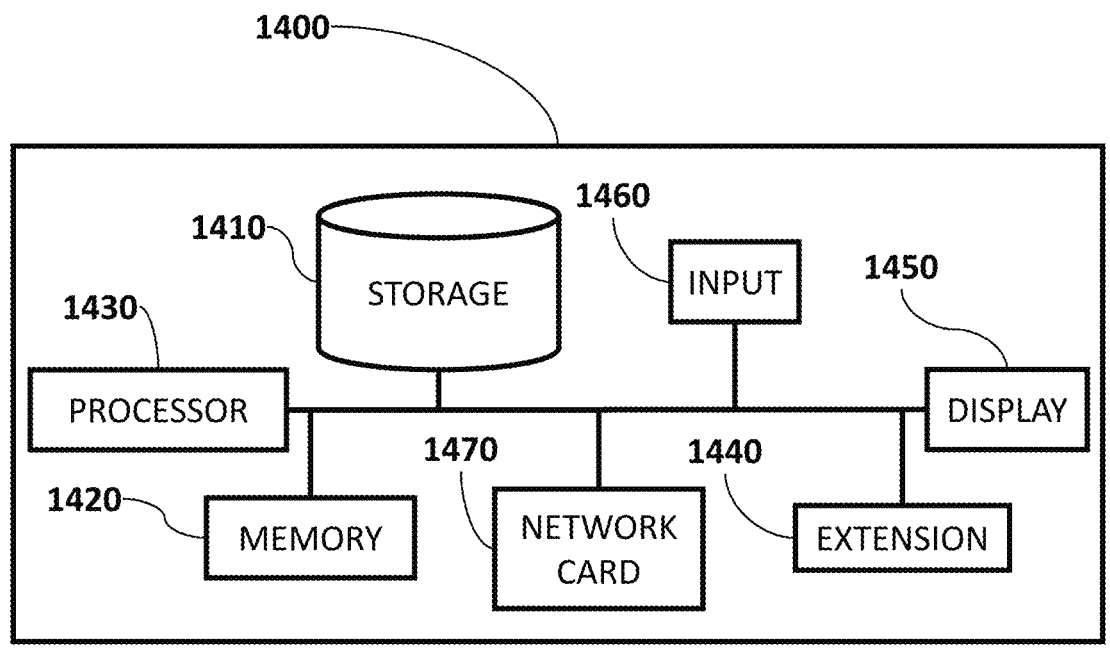
FIG. 14 is a block diagram for a computing device according to aspects of the present disclosure.

FIG. 14 is a block diagram for a computing device 1400 representative of combination of the processor 160, the display 170, the user interface 165, and the memory 175 of FIG. 1 or the controller 245 of FIG. 2 in accordance with embodiments of the present disclosure. The computing device 1400 may include, by way of non-limiting examples, server computers, desktop computers, laptop computers, notebook computers, sub-notebook computers, netbook computers, netpad computers, set-top computers, handheld computers, Internet appliances, mobile smartphones, tablet computers, personal digital assistants, video game consoles, embedded computers, and autonomous vehicles. Those of skill in the art will recognize that many smartphones are suitable for use in the system described herein. Suitable tablet computers include those with booklet, slate, and convertible configurations, known to those of skill in the art.

In embodiments, the computing device 1400 includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In embodiments, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®.

In embodiments, the computing device 1400 may include a storage 1410. The storage 1410 is one or more physical apparatus used to store data or programs on a temporary or permanent basis. In embodiments, the storage 1410 may be volatile memory and requires power to maintain stored information. In embodiments, the storage 1410 may be non-volatile memory and retains stored information when the computing device 1400 is not powered. In embodiments, the non-volatile memory includes flash memory. In embodiments, the non-volatile memory includes dynamic random-access memory (DRAM). In embodiments, the non-volatile memory includes ferroelectric random-access memory (FRAM). In embodiments, the non-volatile memory includes phase-change random access memory (PRAM). In embodiments, the storage 1410 includes, by way of non-limiting examples, CD-ROMs, DVDs, flash memory devices, magnetic disk drives, magnetic tapes drives, optical disk drives, and cloud computing-based storage. In embodiments, the storage 1410 may be a combination of devices such as those disclosed herein.

The computing device 1400 further includes a processor 1430, an extension 1440, a display 1450, an input device 1460, and a network card 1470. The processor 1430 is a brain to the computing device 1400. The processor 1430 executes instructions which implement tasks or functions of programs. When a user executes a program, the processor 1430 reads the program stored in the storage 1410, loads the program on the RAM, and executes instructions prescribed by the program.

The processor 1430 may include a microprocessor, central processing unit (CPU), application specific integrated circuit (ASIC), arithmetic coprocessor, graphic processor, or image processor, each of which is electronic circuitry within a computer that carries out instructions of a computer program by performing the basic arithmetic, logical, control and input/output (I/O) operations specified by the instructions.

In embodiments, the extension 1440 may include several ports, such as one or more universal serial buses (USBs), IEEE 1394 ports, parallel ports, and/or expansion slots such as peripheral component interconnect (PCI) and PCI express (PCIe). The extension 1440 is not limited to the list but may include other slots or ports that can be used for appropriate purposes. The extension 1440 may be used to install hardware or add additional functionalities to a computer that may facilitate the purposes of the computer. For example, a USB port can be used for adding additional storage to the computer and/or an IEEE 1394 may be used for receiving moving/still image data.

In embodiments, the display 1450 may be a cathode ray tube (CRT), a liquid crystal display (LCD), or light emitting diode (LED). In embodiments, the display 1450 may be a thin film transistor liquid crystal display (TFT-LCD). In embodiments, the display 1450 may be an organic light emitting diode (OLED) display. In various embodiments, the OLED display is a passive-matrix OLED (PMOLED) or active-matrix OLED (AMOLED) display. In embodiments, the display 1450 may be a plasma display. In embodiments, the display 1450 may be a video projector. In embodiments, the display may be interactive (e.g., having a touch screen or a sensor such as a camera, a 3D sensor, etc.) that can detect user interactions/gestures/responses and the like.

In still embodiments, the display 1450 is a combination of devices such as those disclosed herein.

A user may input and/or modify data via the input device 1460 that may include a keyboard, a mouse, or any other device with which the use may input data. The display 1450 displays data on a screen of the display 1450. The display 1450 may be a touch screen so that the display 1450 can be used as an input device.

The network card 1470 is used to communicate with other computing devices, wirelessly or via a wired connection. Through the network card 1470, the computing device 1400 may receive, modify, and/or update data from and to a managing server.

The embodiments disclosed herein are examples of the disclosure and may be embodied in various forms. For instance, although certain embodiments herein are described as separate embodiments, each of the embodiments herein may be combined with one or more of the other embodiments herein. Specific structural and functional details disclosed herein are not to be interpreted as limiting, but as a basis for the claims and as a representative basis for teaching one skilled in the art to variously employ the present disclosure in virtually any appropriately detailed structure. Like reference numerals may refer to similar or identical elements throughout the description of the figures.

Any of the herein described methods, programs, algorithms or codes may be converted to, or expressed in, a programming language or computer program. The terms "programming language" and "computer program," as used herein, each include any language used to specify instructions to a computer, and include (but is not limited to) the following languages and their derivatives: Assembler, Basic, Batch files, BCPL, C, C+, C++, C#, Delphi, Fortran, Java, JavaScript, machine code, operating system command languages, Pascal, Perl, PL1, scripting languages, Visual Basic, meta-languages which themselves specify programs, and all first, second, third, fourth, fifth, or further generation computer languages. Also included are database and other data schemas, and any other meta-languages. No distinction is made between languages which are interpreted, compiled, or use both compiled and interpreted approaches. No distinction is made between compiled and source versions of a program. Thus, reference to a program, where the programming language could exist in more than one state (such as source, compiled, object, or linked) is a reference to any and all such states. Reference to a program may encompass the actual instructions and/or the intent of those instructions.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. A method for identifying a vessel within tissue, the method comprising:
   providing a graphical representation of a surgical site;
   grasping the tissue of the patient with first and second jaw members of an end effector including a location sensor;
   illuminating optical light into the grasped tissue via an optical light source disposed on the first jaw member;
   receiving, at a light sensor disposed on the second jaw member, the optical light that has passed through the grasped tissue;
   processing the received light to identify a vessel, which is encompassed within the grasped tissue;
   receiving location information of the end effector from the location sensor;
   synchronizing a location of the identified vessel within the graphical representation based on the location information; and
   displaying the identified vessel at the synchronized location in the graphical representation.

2. The method of claim 1, further comprising:
   supplying energy to the tissue through the end effector to seal the identified vessel;
   illuminating the optical light into the identified vessel after supplying the energy; and
   receiving the optical light that has passed through the identified vessel.

3. The method of claim 2, further comprising:
   processing the received optical light during or after supplying the energy.

4. The method of claim 3, further comprising:
   confirming whether or not the identified vessel is sealed.

5. The method of claim 4, wherein the identified vessel is confirmed to be sealed by comparing the identified vessel before supplying the energy with the identified vessel after supplying the energy.

6. The method of claim 1, wherein the graphical representation is a 3D model or a video image.

7. The method of claim 1, wherein the vessel is selected from the group consisting of a bile vessel, a lymph vessel, and a blood vessel.

8. The method of claim 1, further comprising:
   generating an electromagnetic wave.

9. The method of claim 8, further comprising:
   sensing the electromagnetic wave, wherein the location information is based on the sensed electromagnetic wave.

10. The method of claim 9, wherein the identified vessel is displayed in an augmented manner in the graphical representation.

11. A method for identifying a vessel within tissue, the method comprising:
    receiving, at a light sensor disposed on a first jaw member of an end effector, optical light illuminated by an optical light source disposed on a second jaw member of the end effector and that has passed through tissue grasped between the first and second jaw members;
    processing the received light to identify a vessel, which is encompassed within the grasped tissue;
    receiving location information of the end effector from a location sensor disposed on the end effector;
    synchronizing a location of the identified vessel within a graphical representation of a surgical site based on the location information; and
    displaying the identified vessel at the synchronized location in the graphical representation.

* * * * *